United States Patent
Hwang et al.

(10) Patent No.: US 8,853,264 B2
(45) Date of Patent: Oct. 7, 2014

(54) USE OF LIGNAN COMPOUNDS FOR TREATING OR PREVENTING INFLAMMATORY DISEASE

(75) Inventors: Jae-Kwan Hwang, Gyeonggi-do (KR); Do-Un Kim, Gyeonggi-do (KR); Jae-Youn Chung, Seoul (KR); Hee-Chul Chung, Gyeonggi-do (KR); Kyu-Lee Han, Seoul (KR)

(73) Assignees: Newtree Industry Co., Ltd., Sungnam (KR); Jae-Kwan Hwang, Goyang (KR)

( * ) Notice: Subject to any disclaimer, the term of this patent is extended or adjusted under 35 U.S.C. 154(b) by 0 days.

(21) Appl. No.: 12/766,255

(22) Filed: Apr. 23, 2010

(65) Prior Publication Data
US 2010/0285154 A1 Nov. 11, 2010

Related U.S. Application Data

(63) Continuation-in-part of application No. 11/813,590, filed as application No. PCT/KR2006/000065 on Jan. 6, 2006, now abandoned.

(30) Foreign Application Priority Data

Jan. 7, 2005 (KR) .................. 10-2005-0001761

(51) Int. Cl.
| | | |
|---|---|---|
| A61K 36/185 | (2006.01) | |
| A61K 31/36 | (2006.01) | |
| A61P 17/00 | (2006.01) | |
| A61P 29/00 | (2006.01) | |
| A61K 9/00 | (2006.01) | |
| A61K 9/20 | (2006.01) | |

(52) U.S. Cl.
CPC ............... *A61K 31/36* (2013.01); *A61K 9/0095* (2013.01); *A61K 9/2054* (2013.01); *A61K 36/185* (2013.01); *Y10S 514/859* (2013.01); *Y10S 514/886* (2013.01)
USPC .......... 514/464; 424/725; 424/776; 514/18.6; 514/731; 514/859; 514/886; 549/445

(58) Field of Classification Search
CPC ... A61K 31/36; A61K 36/185; A61K 9/0095; A61K 9/2054
USPC ......... 514/464, 18.6, 731, 859, 886; 549/445; 424/725, 776
See application file for complete search history.

(56) References Cited

PUBLICATIONS

Olajide et al, Biological Effects of *Myristica fragrans* extract, Phyotherapy Research, 13, 344-345, 1999.*

(Continued)

*Primary Examiner* — Savitha Rao
(74) *Attorney, Agent, or Firm* — Joseph Hyosuk Kim; JHK Law

(57) ABSTRACT

The present invention relates to the use of lignan compounds for treating or preventing an inflammatory disease. More particularly, it relates to a method for preventing or treating an inflammatory disease, comprising administering to a subject in need thereof an effective amount of macelignan represented by Chemical Formula I or a pharmaceutically acceptable salt thereof. The lignan compound has the effect of inhibiting inflammatory reactions by inhibiting the production or expression of inflammation mediators NO, iNOS, $PGE_2$, COX-2 and TNF-α and by treating or preventing inflammatory disease in vivo. Accordingly, the lignan compound or a *Myristica fragrans* extract will be highly useful for the treatment or prevention of an inflammatory disease.

1 Claim, 37 Drawing Sheets

(56) References Cited

PUBLICATIONS

Hadir et al, Anti-inflammatory activity of *Myristica fragrans* in acute inflammation, Agris record, Conferene 15, malysian Biochemical Society Conference, Kaula Lumpur, Sep. 3-4, 1990.*

Seon Lee et al, Structure-Activity Relationship of Lignans from *Schisandra chinensis* as Platelet Activating factor antagonists, Biological and Pharmaceutical Bulletin, 22-3, 265-267 (1999).*

Sadhu et al, Chem Pharm Bull. 51 (5) 595-598, 2003.*

* cited by examiner

Fig.10
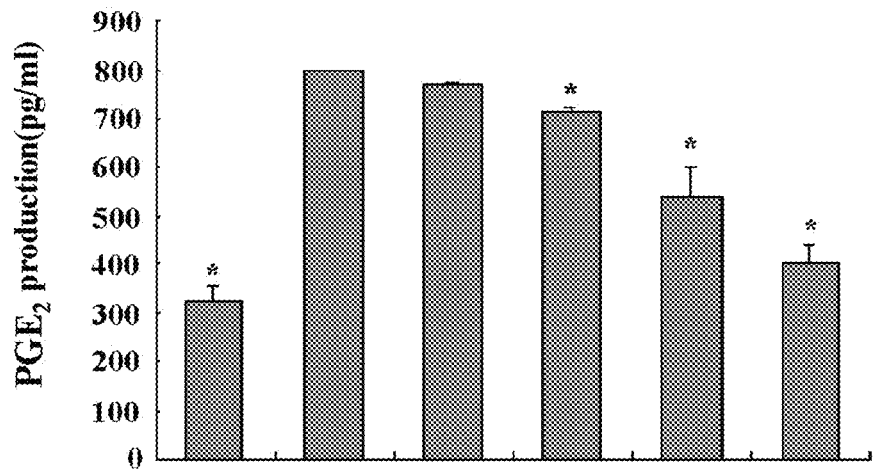
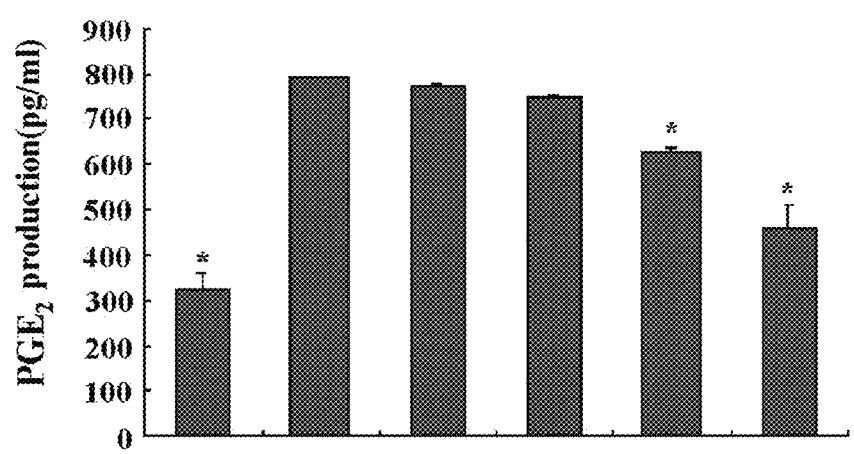

Fig.12
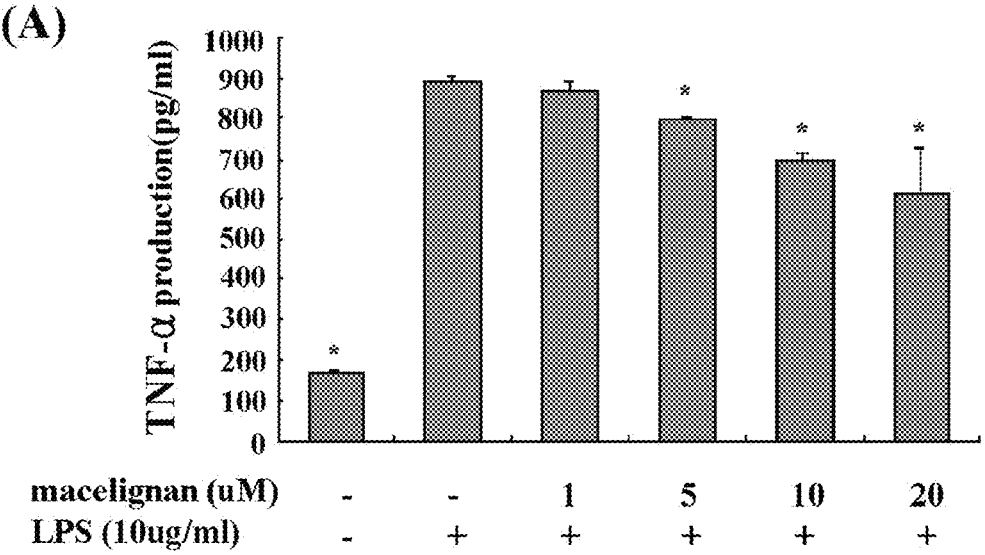
(A)
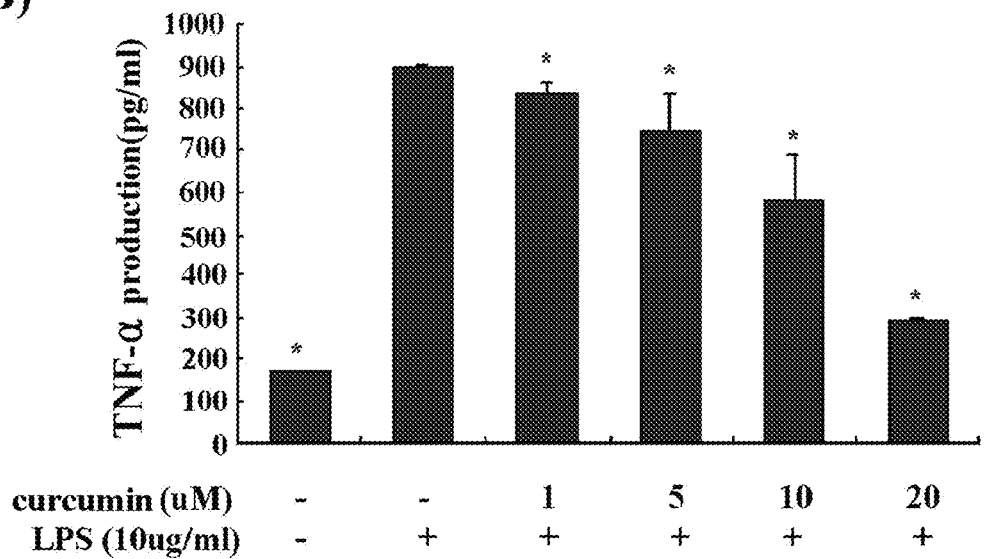
(B)

Fig.13
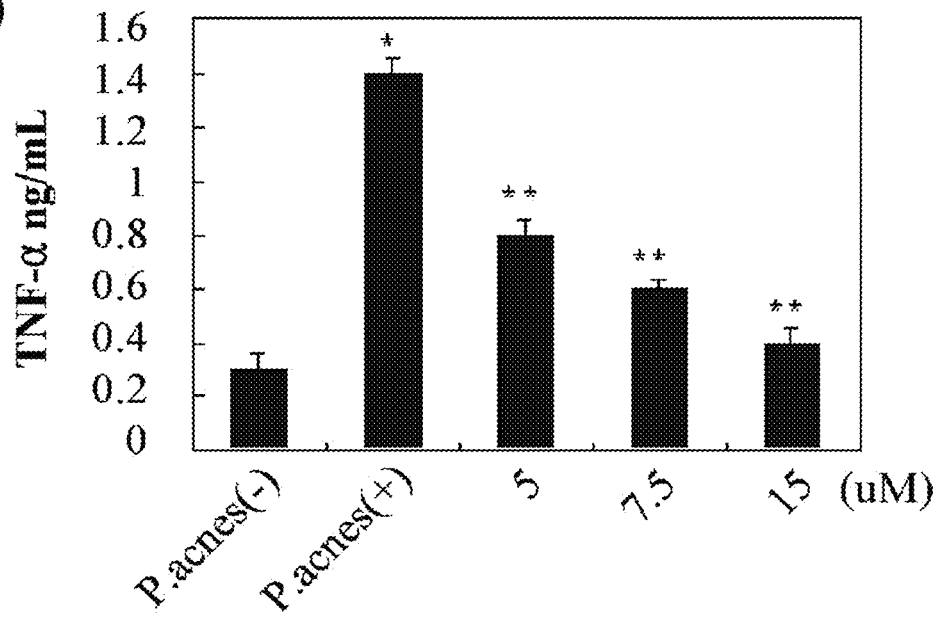
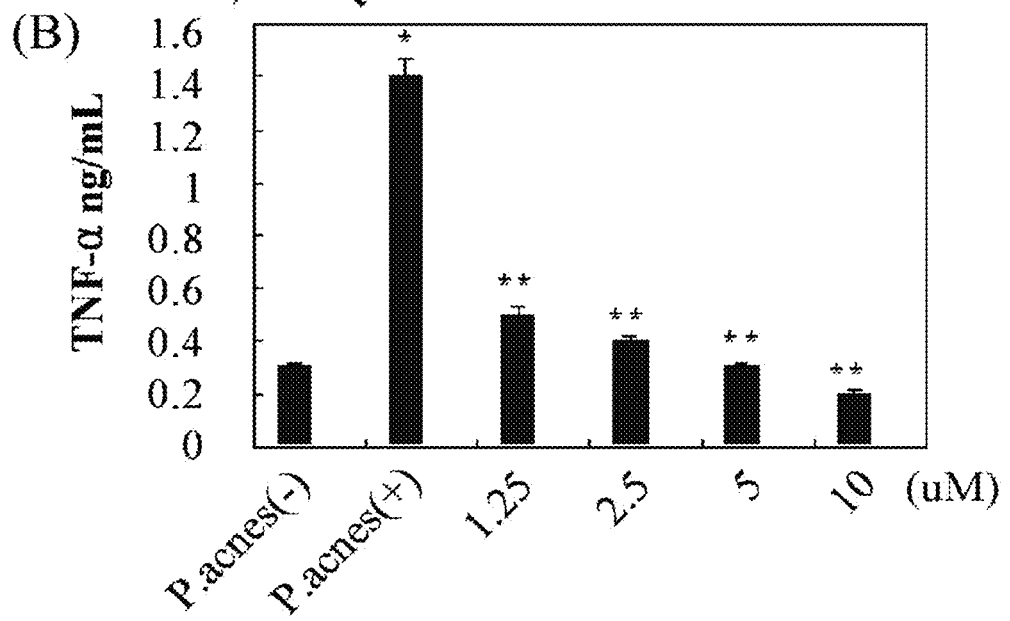

Fig.22
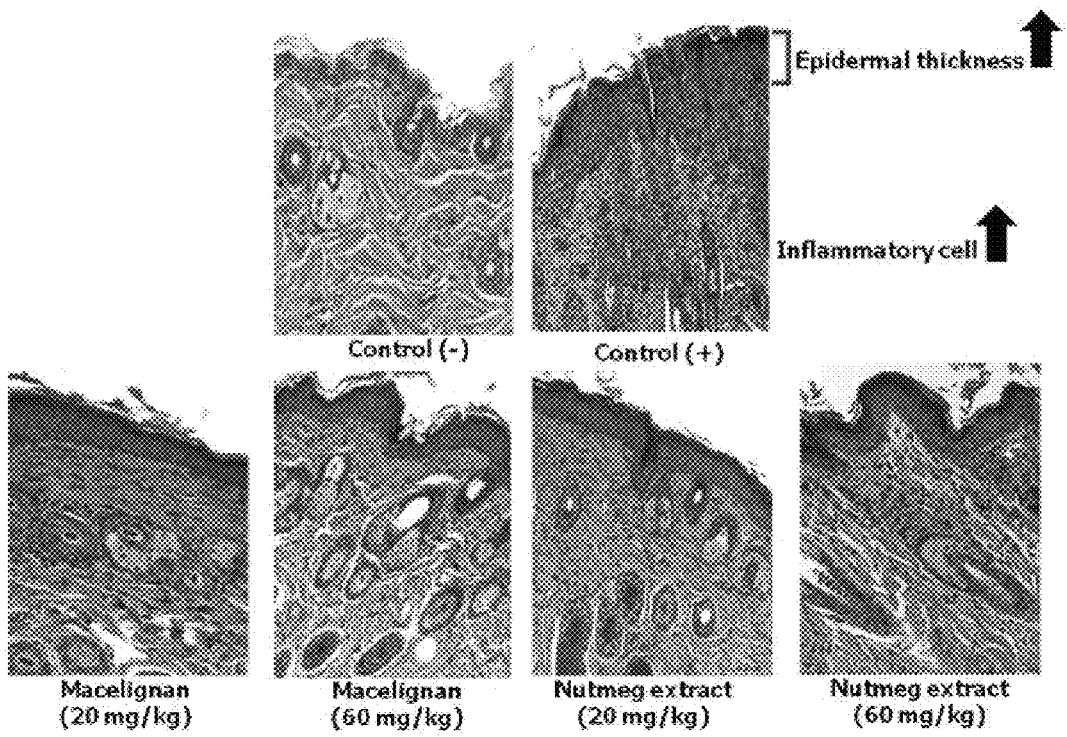
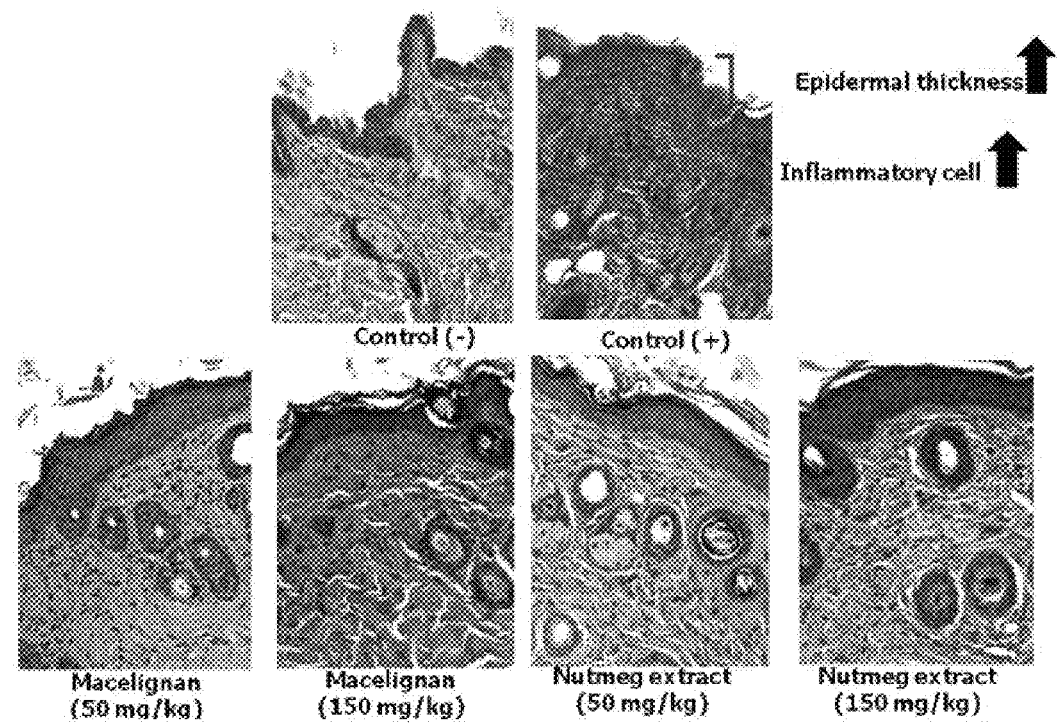

Fig.23
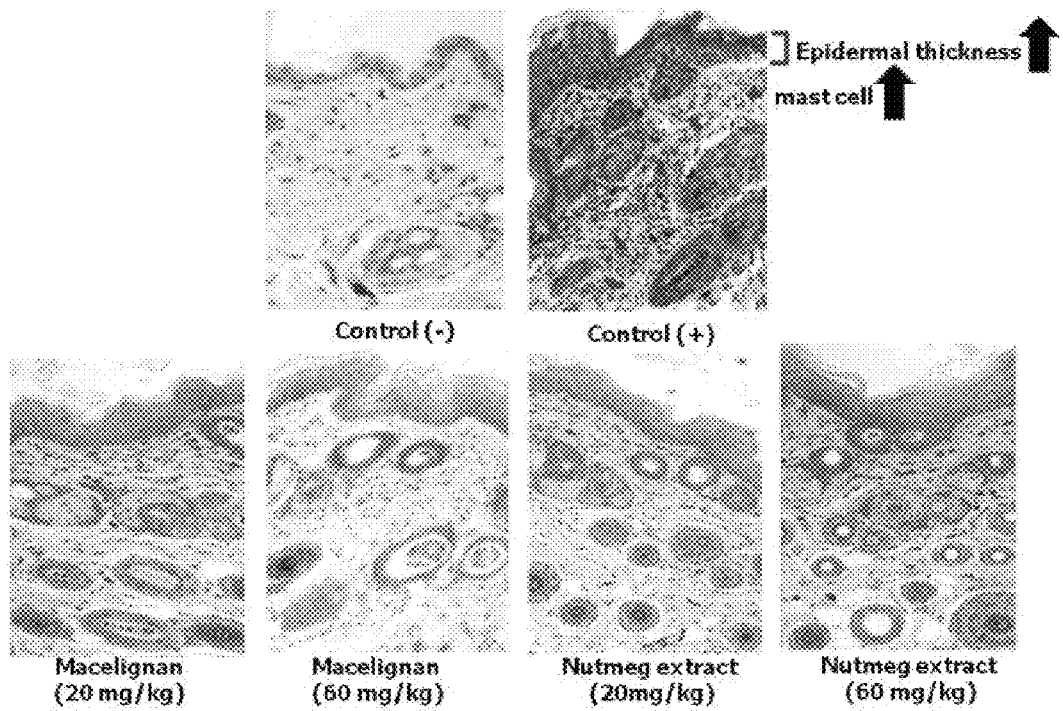
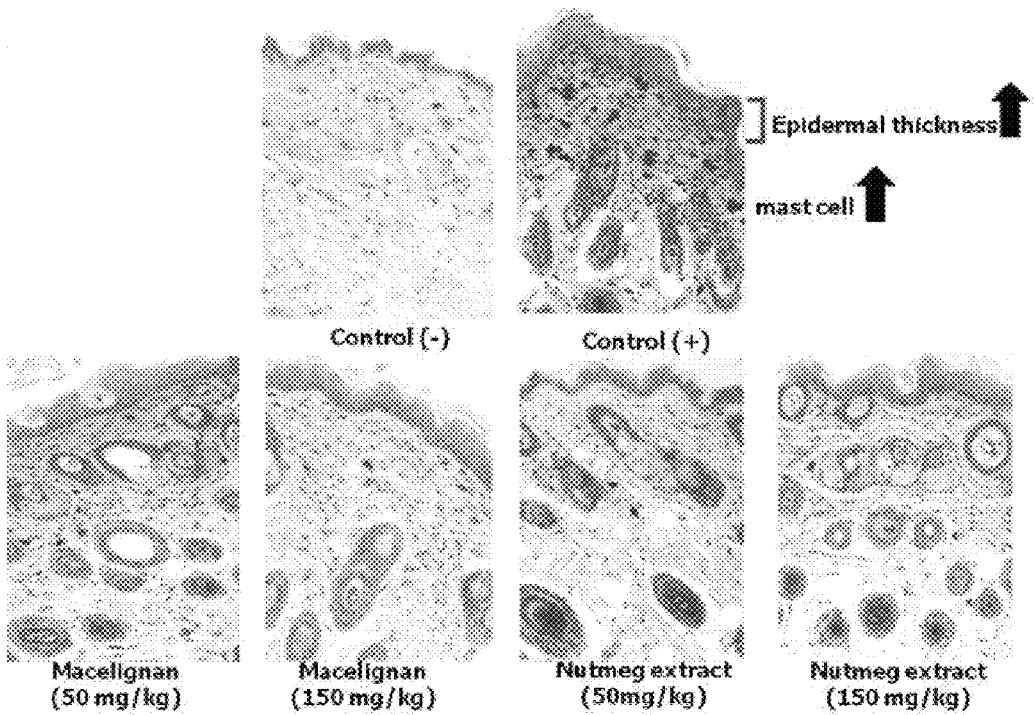

Fig.24
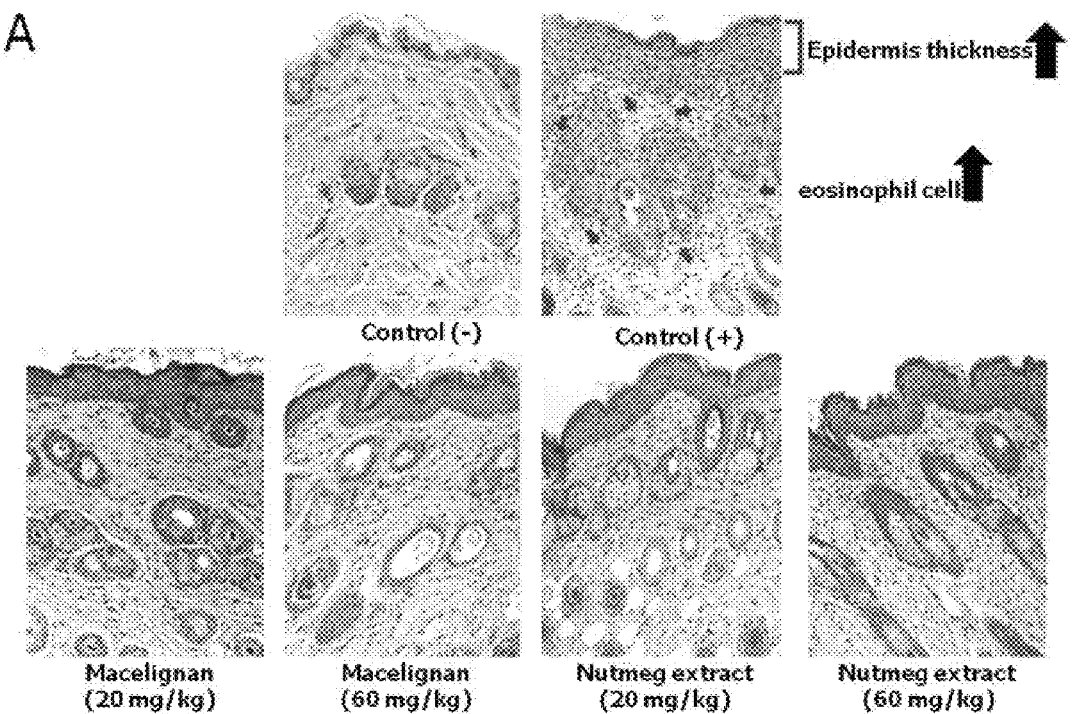
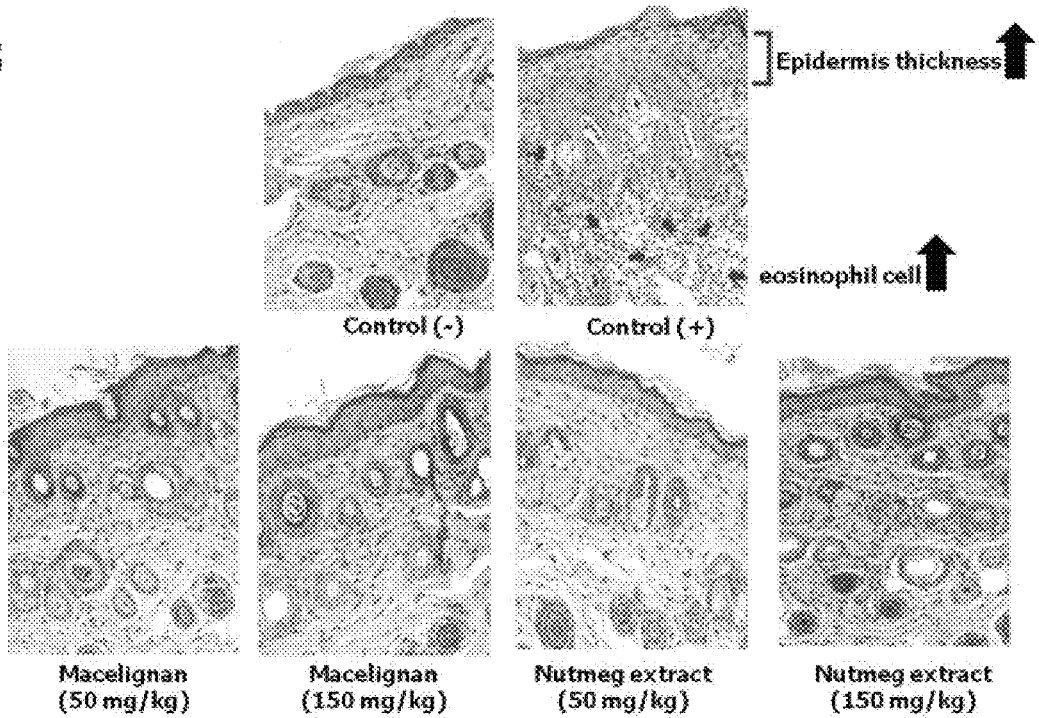

Fig.27
A
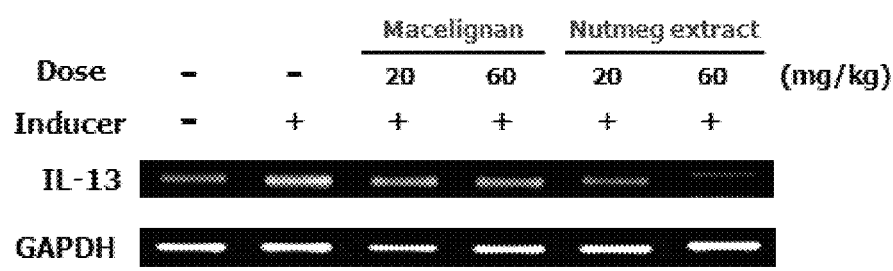
B
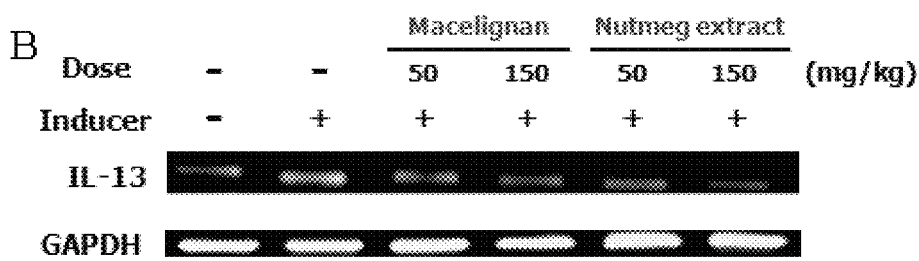

Fig.28
A
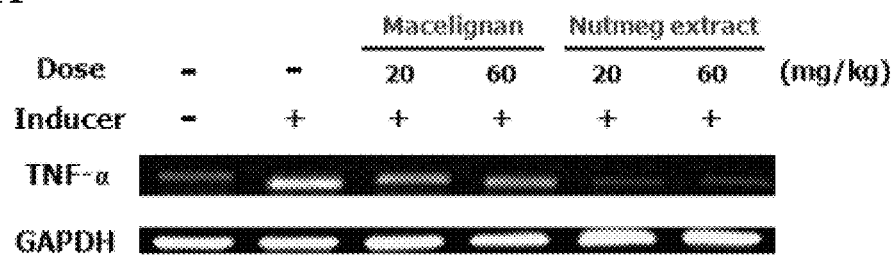
B
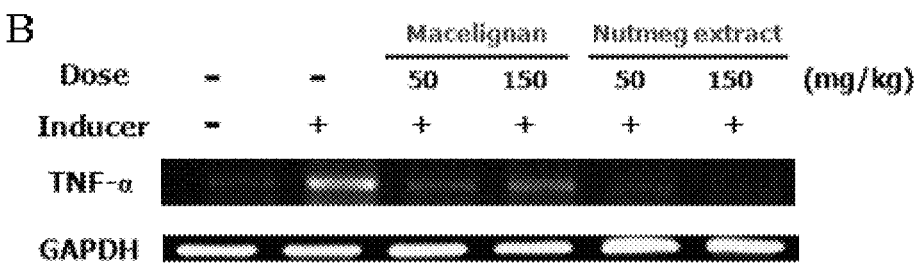

Fig.29
A
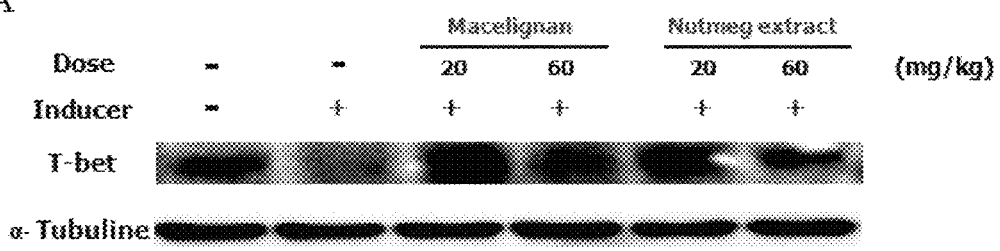
B
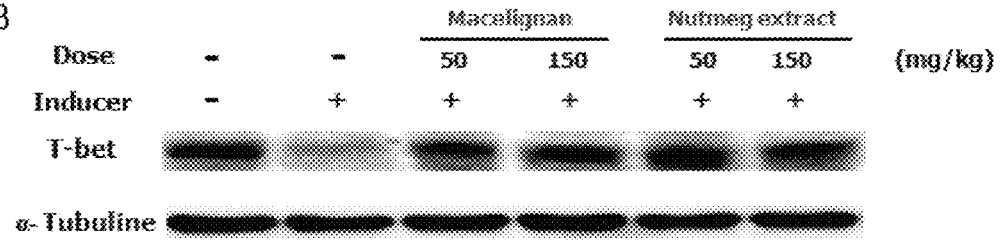

Fig.30
A
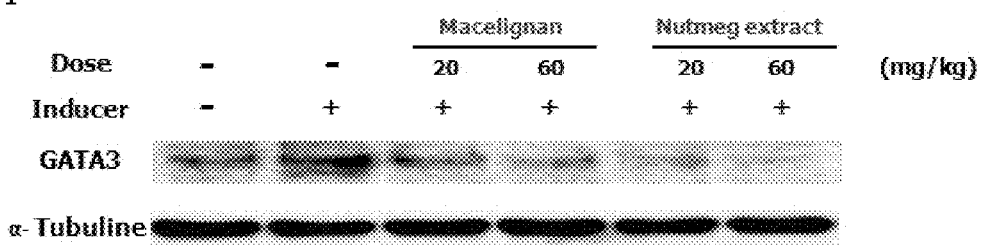
B
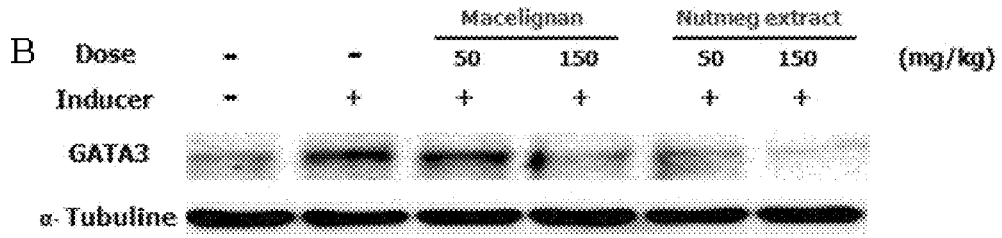

Fig.31
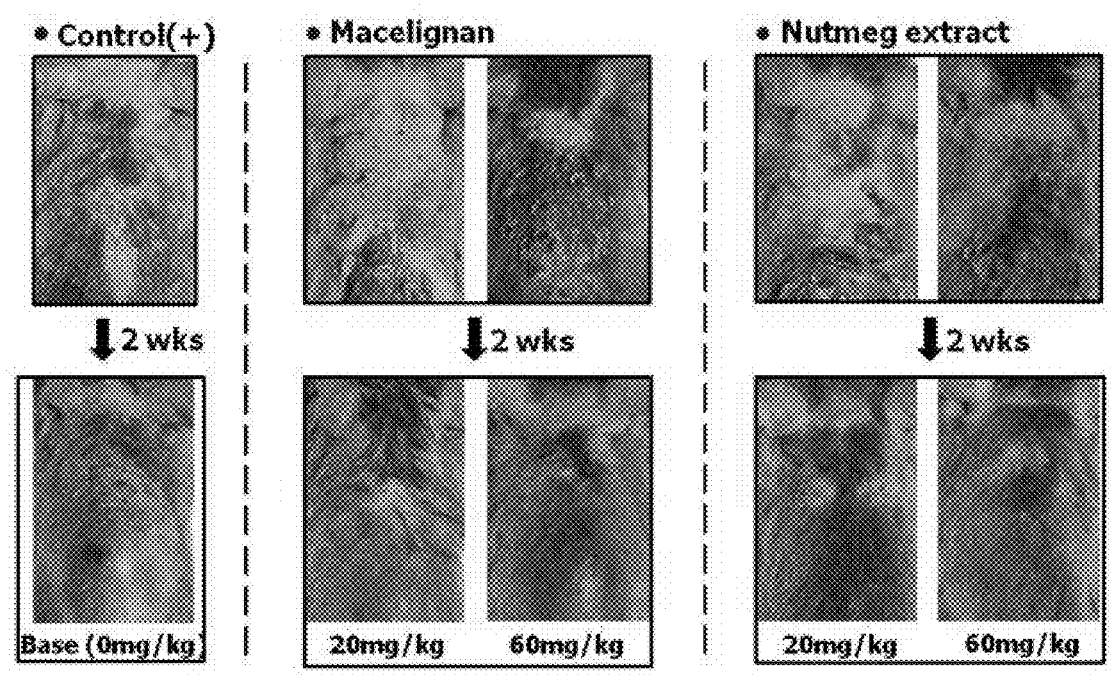
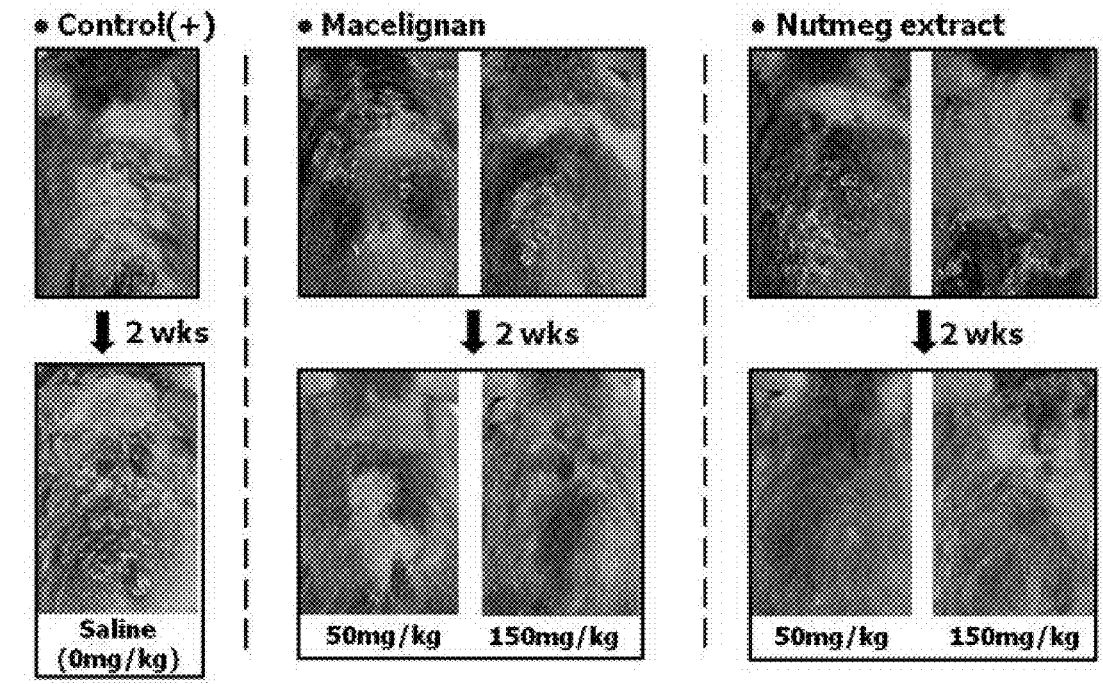

Ach challenge

USE OF LIGNAN COMPOUNDS FOR TREATING OR PREVENTING INFLAMMATORY DISEASE

CROSS-REFERENCE TO RELATED APPLICATIONS

The present application is a continuation-in-part of U.S. patent application Ser. No. 11/813,590, filed Jul. 9, 2007, which is a national phase application under 35 U.S.C. §371, of PCT/KR2006/000065, filed Jan. 6, 2006, which claims the benefit of priority to Korean Patent Application No. KR 10-2005-0001761, filed on Jan. 7, 2005, the contents of which are incorporated by reference herein in their entirety.

FIELD OF THE INVENTION

The present invention relates to the use of macelignan for treating or preventing an inflammatory disease. More particularly, it relates to a method for the treatment or prevention of an inflammatory disease, comprising administering to a subject in need thereof an effective amount of macelignan represented by Chemical Formula I or a pharmaceutically acceptable salt thereof.

BACKGROUND OF THE INVENTION

Inflammatory reactions result from tissue (cell) injury or infection by foreign pathogens and show a series of complex physiological responses such as enzyme activation, inflammation mediator release, body fluid infiltration, cell movement and tissue destruction, and external symptoms such as erythema, edema, pyrexia, pain and etc., in which various inflammation-mediating factors and immune cells in local blood vessels and body fluids are involved. Also, in some cases, these inflammation reactions result in acute inflammation, granuloma, and chronic inflammations such as rheumatoid arthritis and osteoarthritis (Goodwin J. S. et al., *J. Clin. Immunol.*, 9: 295-314, 1989).

Among enzymes having important effects on blood coagulation and inflammation, cyclooxygenase (hereinafter, referred to as 'COX') produces two main products, i.e., prostaglandin and thromboxane. Prostaglandin is an unsaturated fatty acid having various physiological activities and acts as local hormones or cell function regulators in the human body, such as inflammation and pain transmission, vasodilation, body temperature regulation, and gastric secretion stimulation (Marnett, L. J. et al., *J. Biol. Chem.*, 274: 22903-22906, 1999). COX-1 plays an important role in the maintenance of cell homeostasis by maintaining normal physiological responses, such as gastrointestinal tract protection, renal blood flow regulation and platelet aggregation. Meanwhile, in a process wherein inflammation caused by external stimulus is transmitted, inducible isoenzyme COX-2 is temporarily expressed to release an excessive amount of prostaglandin at the site where inflammation occurs. Prostaglandin causes erythema, edema and pain, the main symptoms of inflammation, and has an activity of increasing the action of endogenous inflammatory mediator histamine, and the like. Thus, the inhibition of prostaglandin production at inflammatory sites can give much help in the treatment of inflammation.

Currently commercially available non-steroidal anti-inflammatory drugs (NSAIDs) aspirin, indomethacin, naproxen, ibuprofen and the like show anti-inflammatory effects by suppressing prostaglandin production through the inhibition of activity of COX-2 enzyme (Meade E. A. et al., *J. Biol. Chem.*, 268: 6610, 1993). However, these NSAID drugs have problems in that they also inhibit COX-1 from playing an important role in maintaining the normal function of gastrointestinal tract and renal platelet, in addition to inhibiting COX-2 temporarily expressed by inflammatory stimulus, and thus cause severe side-effects, such as gastrointestinal tract bleeding and renal failure (Surh Y. J. et al., *Mutation Research* 480-481: 243-268, 2001). Accordingly, it is very important from an industrial point of view to find a natural substance that provides anti-inflammatory action while minimizing side effects.

Meanwhile, lignan refers to a group of natural compounds comprising n-phenyl propane bound to the β-position of the n-propyl side chain and is widely distributed in nature. There have been studies on the various physiological activities of lignan, such as blood glucose-lowering action, anticancer action, anti-asthmatic action and whitening action. For example, it was reported that lignans isolated from sesame, such as sesamin, episesamin, sesaminol, sesamolin and episesaminol, have anti-inflammatory effects (Korean Patent Laid-Open Publication No. 1997-7001043), and lignan compounds isolated from Magnoliae flos can be used as anti-asthmatic agents (Korean Patent Registration No. 0263439). Moreover, macelignan is a typical lignan compound found in *Myristica fragrans* (Tuchinda P. et al., Phytochemistry, 59: 169-173, 2002), and was reported to have various activities, such as the activation of caspase-3 inducing apoptosis (Park B. Y. et al., *Biol. Pharm. Bull.*, 27(8): 1305-1307, 2004), and antioxidant action (Sadhu, S. K. et al., *Chem. Pharm. Bull.*, 51(9): 595-598, 2003). However, there is still no report on the anti-inflammatory activity of lignan compounds, including macelignan.

DETAILED DESCRIPTION OF THE INVENTION

Technical Problem

Accordingly, the present inventors have conducted a long-term investigation to find a naturally derived compound having anti-inflammatory activity and, as a result, found that a lignan compound isolated and purified from a *Myristica fragrans* extract shows excellent anti-inflammatory activity, thereby completing the present invention.

It is an object of the present invention to provide the use of lignan compounds for treating or preventing inflammatory disease.

Technical Solution

To achieve the above object, in one aspect, the present invention provides a method for preventing or treating an inflammatory disease, comprising administering to a subject in need thereof an effective amount of macelignan represented by Chemical Formula I or a pharmaceutically acceptable salt thereof:

[Chemical Formula I]

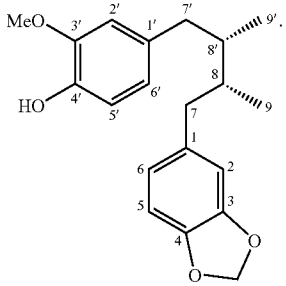

In another aspect, the present invention provides a method for preventing or treating an inflammatory disease, comprising administering to a subject in need thereof an effective amount of water or a $C_1$-$C_6$ organic solvent extract of *Myristica fragrans*.

As used herein, the term "effective amount" refers to the amount of the inventive lignan compound, which can effectively treat an inflammatory disease when being administered to a subject.

Also, as used herein, the term "subject" encompasses mammals, particularly animals including human beings. The subject may be a patient in need of treatment.

Hereinafter, the present invention will be described in detail.

The present invention is characterized by providing a novel use of lignan compound isolated and purified from a *Myristica fragrans* extract.

The lignan compound according to the present invention may be macelignan represented by Chemical Formula I, i.e., [(8R,8'S)-7-(3,4-methylenedioxyphenyl)-7'-(4-hydroxy-3-methoxyphenyl)-8,8'-dimethylbutane)]:

[Chemical Formula 1]

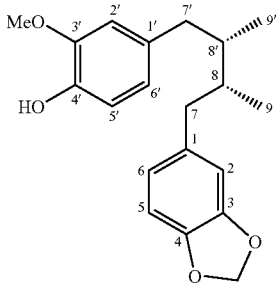

The lignan compound according to the present invention may be used in the form of a salt, and preferably a pharmaceutically acceptable salt. Preferably, the salt is the acid-addition salt formed by a pharmaceutically acceptable free acid. The free acid used in the present invention may be organic acids and inorganic acids. The organic acids include, but are not limited to, citric acid, acetic acid, lactic acid, tartar acid, maleic acid, fumaric acid, formic acid, propionic acid, oxalic acid, trifluoroacetic acid, benzoic acid, gluconic acid, methane sulfonic acid, glycolic acid, succinic acid, 4-toluene sulfonic acid, glutamic acid and aspartic acid. Also, the inorganic acids include, but are not limited to, hydrochloric acid, bromic acid, sulfuric acid and phosphoric acid.

The inventive lignan compound can be obtained from a plant or part of a plant according to any conventional method for extracting and isolating substance. Stems, roots or leaves are suitably dehydrated and macerated or only dehydrated in order to obtain the desired extract, which is then purified using any conventional purification method known to a person skilled in the art. Synthetic compounds or their derivatives corresponding to the lignan compound represented by Chemical Formula I are generally commercially available substances or they may be manufactured using any known synthetic method.

The inventive lignan compound represented by Chemical Formula I may be isolated and purified from *Myristica fragnance* Houtt (Jung Yun Lee et al., *Kor. J. Pharmacogn.* 21(4): 270-273, 1990; Masao Hattori et al., *Chem. Pharm. Bull.*, 34(9):3885-3893, 1986; Masao Hattori et al., *Chem. Pharm. Bull.*, 35(2):668-674, 1987). Preferably, it may be isolated and purified from nutmeg or aril. The nutmeg refers to the ripe fruit of *Myristica fragnance* or a seed contained in the fruit. Moreover, the inventive lignan compound may also be isolated and purified from oil obtained by squeezing nutmeg. Also, it may be isolated and purified from *Myristica argentea* Warb, another member of the Myristicaceae family (Filleur, F. et al., *Natural Product Letters*, 16: 1-7, 2002). In addition, it may also be isolated and purified from *Machilus thunbergii* (Park B. Y. et al., *Biol. Pharm. Bull.*, 27(8): 1305-1307, 2004), and *Leucas aspera* (Sadhu, S. K. et al., *Chem. Pharm. Bull.*, 51(9): 595-598, 2003).

An extraction solvent for isolating the inventive lignan compound may be water or a $C_1$-$C_6$ organic solvent. Preferred examples of the extraction solvent may include purified water, methanol, ethanol, propanol, isopropanol, butanol, acetone, ether, benzene, chloroform, ethyl acetate, methylene chloride, hexane, cyclohexane, petroleum ether and the like, which can be used alone or a mixture thereof. More preferably, methanol or hexane may be used. The isolation and purification of the inventive lignan compound from an extract of *Myristica fragnance* may be performed by one or combination of, for example, column chromatography and high-performance liquid chromatography (HPLC), packed with various synthetic resins, such as silica gel or activated alumina. However, the method for isolating and extracting the active ingredient needs not to be limited to these chromatography techniques.

As such, the inventive lignan compound may be used in the form of an isolated and purified compound or in the form of an extract containing the compound. As described above, the inventive lignan compound may be used in the form of an extract of the seed or fruit of *Myristica fragnance* or an aril extract, or in the form of oil obtained by squeezing the seed of *Myristica fragnance*. As described above, the extract can be obtained by extracting *Myristica fragnance* with water or a $C_1$-$C_6$ organic solvent. Preferably, the extract may be an extract of the seed of *Myristica fragnance*, namely, a nutmeg extract.

The inventive lignan compound has anti-inflammatory activity by inhibiting various substances that mediate inflammatory reactions.

Nitric oxide (NO), which is a substance involved in nervous system transmission, relaxation of blood vessel, and cell-mediated immune responses, is produced from L-arginine by NOS (nitric oxide synthase) (Nathan and Xie, 1994; Alderton et al., 2001). Particularly when macrophages are stimulated by IFN-γ or LPS (lipopolysaccaride), iNOS (inducible nitric oxide synthase) will be expressed and a large amount of NO will be produced by the iNOS. It was shown that the inventive lignan compound concentration-dependently inhibited the production of NO in macrophages and the expression of iNOS involved in the production of NO (see FIGS. 8 and 9).

Also, COX-2 is a substance involved in inflammatory responses in vivo and produces inflammatory prostaglandin (PG). The expression of COX-2 is induced by endotoxin LPS secreted by bacteria, and inflammatory cytokines IL-1, TNF-α, IFN-γ and the like. The inventive lignan compound has the effects of inhibiting the expression of COX-2 and also inhibiting the production of $PGE_2$ (prostaglandin E2), a member of PE family, in a concentration-dependent manner (see FIGS. 10 and 11).

TNF-α (tumor necrosis factor α) is a major mediator of acute inflammatory reactions caused by gram-negative bacteria and other infectious microorganisms. Macrophages stimulated by LPS increase the synthesis of TNF-α. In biological action, TNF-α acts on leukocytes and epithelial cells at low concentrations so as to induce acute inflammation. At moderate concentrations, it mediates systemic inflammatory reactions, and at high concentrations, it causes death by pathological abnormality of septic shock. Also, TNF-α produces fever by increasing the synthesis of PG, and causes vascular plugging by inhibiting the expression of thrombomodulin (Abbas and Lichtman, "Cellular and Molecular Immunology" the fifth edition. pp. 247-253, 2003). The inventive lignan compound has the effect of inhibiting the production of TNF-α in macrophages and human monocytic cells (see FIGS. 12 and 13).

The present inventors applied the inventive lignan compound locally on the ears of rats having edema induced by treatment with TPA (12-O-tetradecanoylphorbol-13-acetate). As a result, the inventive lignan compound inhibited the formation of edema in a concentration-dependent manner and showed a percent edema inhibition higher than that of currently commercially available anti-inflammatory drug indomethacin (see Table 2). Also, the present inventors prepared creams comprising the lignan compound and applied the creams locally on the ears of rats. As a result, the creams greatly inhibited the formation of edema (see Table 4).

Meanwhile, the present inventors applied *Myristica fragnance* extracts (methanol and hexane crude extracts) locally on the ears of rats having edema by treatment with TPA. As a result, it could be observed that the extracts inhibited the formation of edema in a concentration-dependent manner (see Table 5).

These results suggest that the inventive lignan compound shows excellent anti-inflammatory action by inhibiting not only COX-2, but also various factors that mediate inflammation reactions. Also, the results indicate that the *Myristica fragnance* extract can show the same anti-inflammatory effect even by itself. The anti-inflammatory activities of the inventive lignan compound represented by Chemical Formula I and of the *Myristica fragnance* extract were found for the first time in the present invention.

In view of the fact that currently commercially available non-steroidal anti-inflammatory drugs mostly show anti-inflammatory effects by inhibiting the activity of COX-2 enzyme, it can be seen that the inventive lignan compound can be used as an anti-inflammatory drug having a higher effect than those of the prior anti-inflammatory drugs.

Accordingly, the present invention provides a pharmaceutical composition for the treatment or prevention of an inflammatory disease, which contains the lignan compound of represented by Chemical Formula I or a pharmaceutically acceptable salt thereof as an active ingredient. Also, the present invention provides a pharmaceutical composition for the treatment or prevention of an inflammatory disease, which contains the *Myristica fragnance* extract as an active ingredient. The preparation of the *Myristica fragnance* extract is performed in the same manner as described above.

Furthermore, the present invention provides a method for preventing or treating an inflammatory disease, the method comprising administering to a subject in need thereof an effective amount of the compound of represented by Chemical Formula I or a pharmaceutically acceptable salt thereof.

In addition, the present invention provides the use of the lignan compound of represented by Chemical Formula I for preparing a pharmaceutical composition for the prevention or treating an inflammatory disease.

The inventive lignan compound or a pharmaceutically acceptable salt thereof can be administered orally or parenterally and used in form of common drug formulations. The common drug formulations may be prepared using fillers, thickeners, binders, wetting agents, disintegrants, and diluents such as surfactants, or excipients. Solid formulations for oral administration include tablets, pills, powders, granules, and capsules and are prepared by combining the lignan compound or the *Myristica fragnance* extract with at least one excipient, for example, starch, calcium carbonate, sucrose, lactose or gelatin. Also, except the simple excipient, lubricant such as magnesium stearate or talc may be used. Examples of liquid formulations for oral administration include suspensions, liquids, emulsions and syrups. The liquid formulations may comprise a simple diluent such as water, liquid paraffin, and various excipients, for example, humectants, sweet agents, aromatic agents and preservatives. Examples of pharmaceutical formulations for parenteral administration include sterilized aqueous solutions, non-aqueous solutions, suspensions, emulsions, freeze-dried preparations, ointments and creams. The non-aqueous solutions and suspensions may be prepared using propylene glycol, polyethylene glycol, vegetable oils such as olive oil, and injectable esters such as ethyloleate.

Also, the inventive lignan compound or a pharmaceutically acceptable salt thereof may be administered by parenteral rotes, including subcutaneous, intravenous, intramuscular or intraperitoneal injection. For parenteral administration, the lignan compound of represented by Chemical Formula I or the *Myristica fragnance* extract may be mixed with a stabilizer or buffer in water to prepare a solution or suspension, which may then be provided as ampules or vials each containing a unit dosage form. The dosage units can contain, for example, 1, 2, 3, or 4 times of an individual dose or ½, ⅓ or ¼ times of an individual dose. An individual dose preferably contains the amount of an effective drug which is given in one administration and which usually corresponds to a whole, a half, a third or a quarter of a daily dose.

The inventive lignan compound of represented by Chemical Formula I or the *Myristica fragnance* extract can be administered in an effective dosage of 0.1-50 mg/kg, and preferably 1-10 mg/kg, 1-3 times a day. The dosage of the inventive compound or extract may vary depending on, for example, the body weight, age, sex, health condition, diet, time of administration, method of administration, excretion rate and disease severity for a certain patient.

The inventive lignan compound was tested for toxicity in oral administration to rats, and as a result, it was observed that the 50% lethality (LD50) was more than 2,000 mg/kg.

Particularly, the inventive pharmaceutical composition comprising the lignan compound or the *Myristica fragnance* extract can be formulated in the form of drugs for skin application, i.e., ointments and creams, and it may be properly combined by the form of drugs in the range of 0.001-10.0 wt %, and preferably 0.005-5.0 wt %, based on the total weight of a formulation. If the composition is used in an amount of less than 0.005 wt %, it will provide low anti-inflammatory activity, and if it is added in an amount of more than 10 wt %, it will show no significant difference in anti-inflammatory activity only increasing an additive.

The present invention, the term "inflammatory disease" refers to a disease involving an inflammation caused by various stimulative factors, such as NO, iNOS, COX-2, $PGE_2$ and TNF-α, that induce a series of inflammatory reactions. Examples of the inflammatory disease include, but are not limited to, common inflammatory symptoms such as osteoarthritis, infectious arthritis, post-infectious arthritis, gonococcal arthritis, tuberculous arthritis, viral arthritis, fungal arthritis, syphilitic arthritis, Lyme disease, arthritis associated with "vasculitic syndromes", non-articular rheumatism, rheumatoid arthritis, bronchial asthma, asthma and atopic dermatitis

BRIEF DESCRIPTION OF THE DRAWINGS

FIG. 10 shows analysis results for the PGE$_2$ production-inhibitory effects of the inventive lignan compound (A) and Curcumin (B).

FIG. 12 shows analysis results for the TNF-α production-inhibitory effects of the inventive lignan compound (A) and curcumin (B) in macrophages stimulated by LPS.

FIG. 13 shows analysis results for the TNF-α production-inhibitory effects of the inventive lignan compound (A) and indomethacin (B) in human monocyte U937 cells stimulated by *P. acnes*.

FIG. 22 shows the result of H&E staining by skin application (A) and oral administration (B) of macelignan and nutmeg extract.

FIG. 23 shows the result of Toluidine blue staining by skin application (A) and oral administration (B) of macelignan and nutmeg extract.

FIG. 24 shows the result of Congo red staining by skin application (A) and oral administration (B) of macelignan and nutmeg extract.

FIG. 27 shows the change in IL-13 mRNA level in skin lesion by skin application (A) and oral administration (B) of macelignan and nutmeg extract.

FIG. 28 shows the change in TNF-α mRNA level in skin lesion by skin application (A) and oral administration (B) of macelignan and nutmeg extract.

FIG. 29 shows the change in T-bet expression level in spleen by skin application (A) and oral administration (B) of macelignan and nutmeg extract.

FIG. 30 shows the change in GATA-3 expression level in spleen by skin application (A) and oral administration (B) of macelignan and nutmeg extract.

FIG. 31 shows the result of clinical visual evaluation by skin application (A) and oral administration (B) of macelignan and nutmeg extract.

BEST MODE FOR CARRYING OUT THE INVENTION

Figure 1:
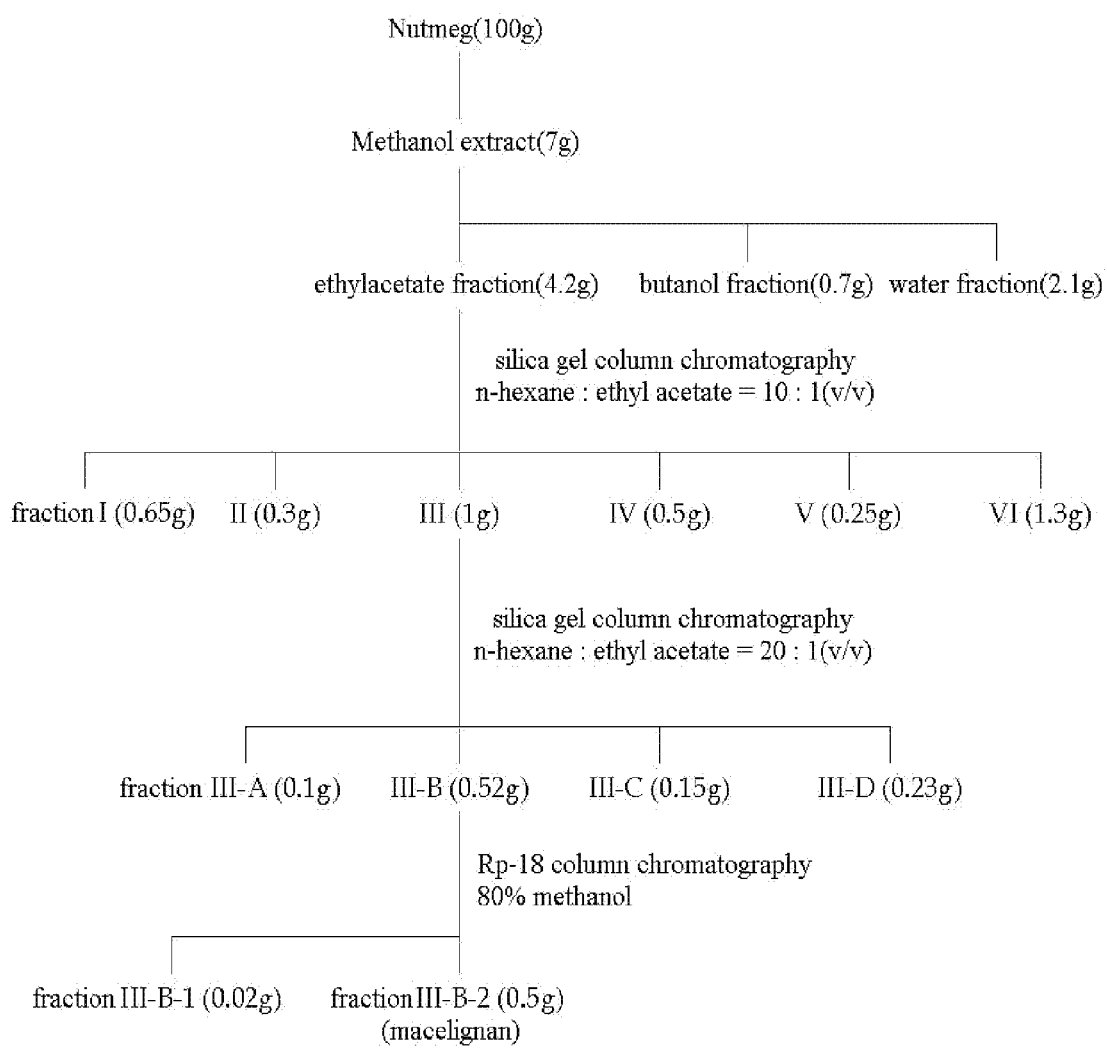
FIG. 1 shows a process of isolating a lignan compound from *Myristica fragrans*.

Hereinafter, the present invention will be described in detail by examples. It is to be understood, however, that these examples are for illustrative purpose only and are not construed to limit the scope of the present invention. In these examples and test examples, percentages are by weight unless otherwise specified. Activity analysis was repeated at least three times, and the results were expressed as mean±standard deviation. Also, statistical analysis was performed by Student's t-test, and a value of p<0.05 was considered statistically significant.

Example 1

Isolation and Purification of Lignan Compound from *Myristica fragrans*

<1-1> Isolation and Purification of Lignan Compound

To 100 g (dry weight) of dried and crushed nutmeg, 400 ml of 75-vol % methanol was added, and the solution was left to stand at room temperature for 2 days. The solution was then filtered through Whatman filter paper No. 2. The filtration step was repeated two times. The methanol filtrate was concentrated under vacuum and lyophilized to prepare 7 g of a methanol crude extract of nutmeg. The methanol crude extract was fractionated sequentially with ethyl acetate, butanol and water to obtain 4.2 g of an ethyl acetate fraction. The ethyl acetate fraction was eluted by silica gel column chromatography (Merck Kieselgel 66; 70-230 mesh) with a mixed solvent of hexane and ethyl acetate (10:1 v/v) to obtain 0.1 g of fraction III. The solvent was completely removed with a vacuum rotary evaporator to prepare a crude extract of nutmeg. Then, the fraction III was eluted by silica gel column chromatography (Merck Kieselgel 66; 70-230 mesh) with a mixed solvent of hexane and ethyl acetate (20:1 v/v) to obtain 0.52 g of fraction III-B. The fraction III-B was eluted by Rp-18 column chromatography (Merck LiChroprep; 25-40

μm) with 80% methanol to obtain 0.5 g of single material fraction III-B-2. This isolation process was shown in FIG. 1.

<1-2> Analysis of Structure

Figure 2:
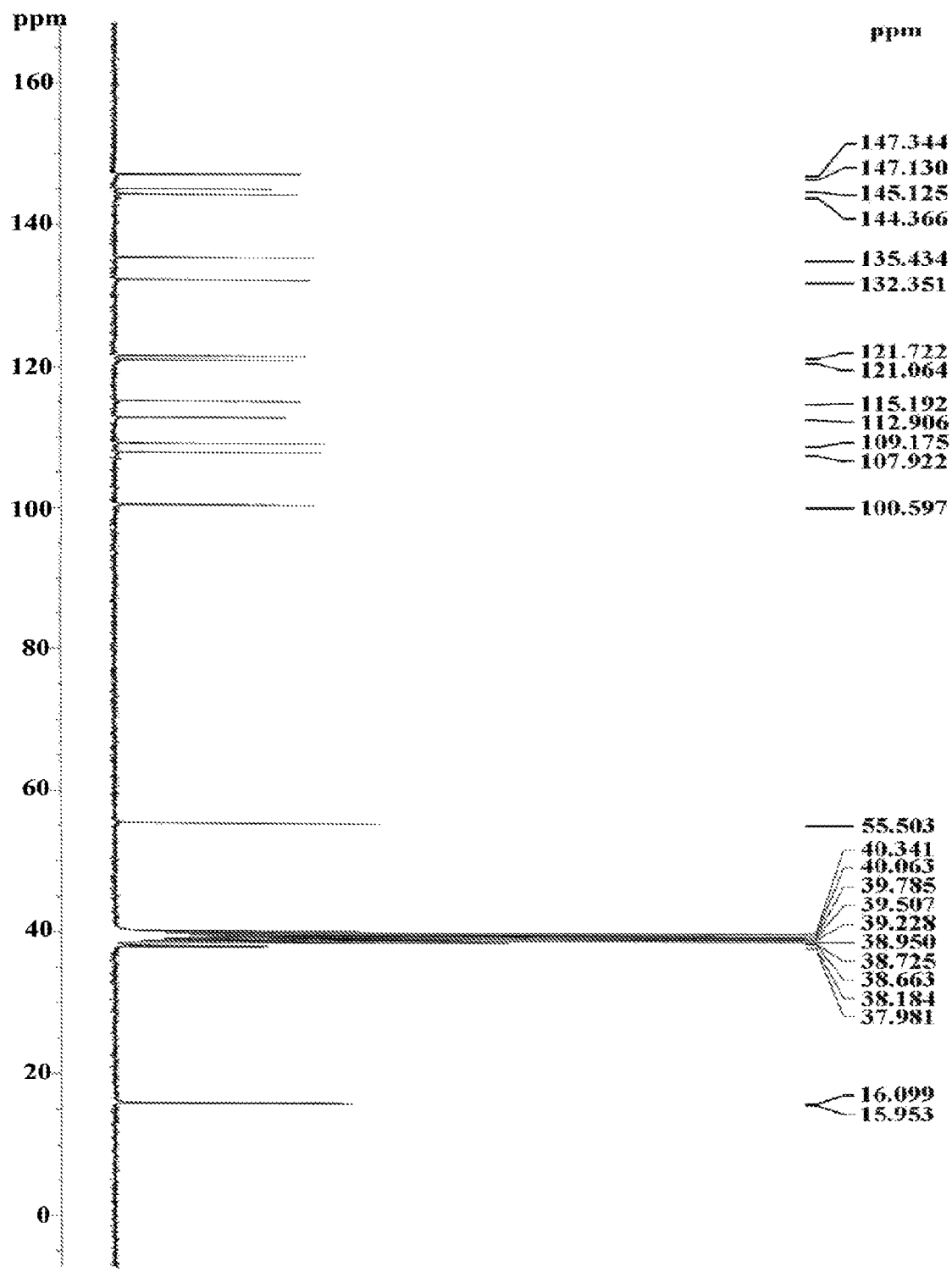
FIG. 2 shows the $^{13}$C-NMR spectrum of the inventive lignan compound.
Figure 3:
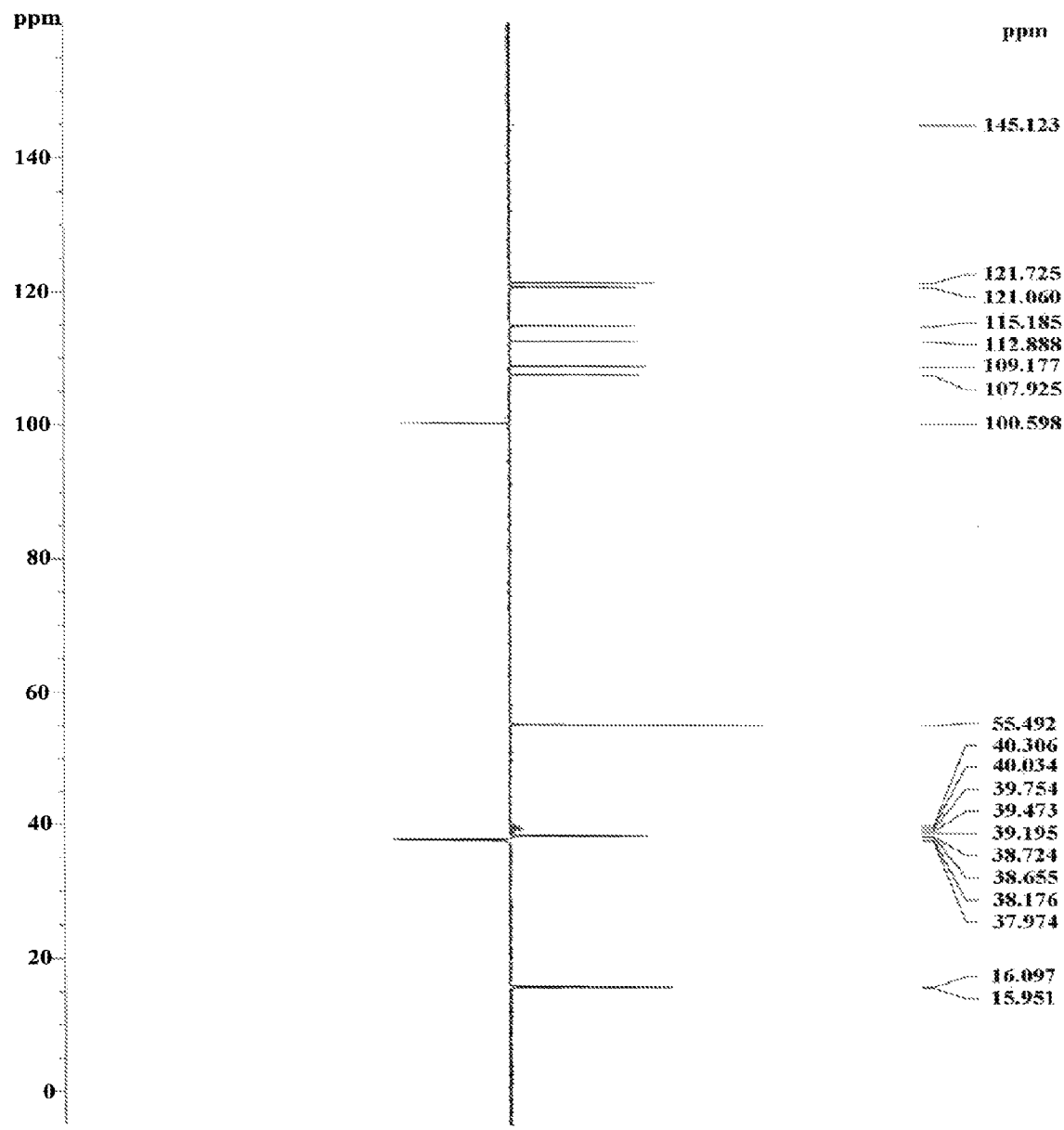
FIG. 3 shows the $^1$H-NMR spectrum of the inventive lignan compound.
Figure 4:
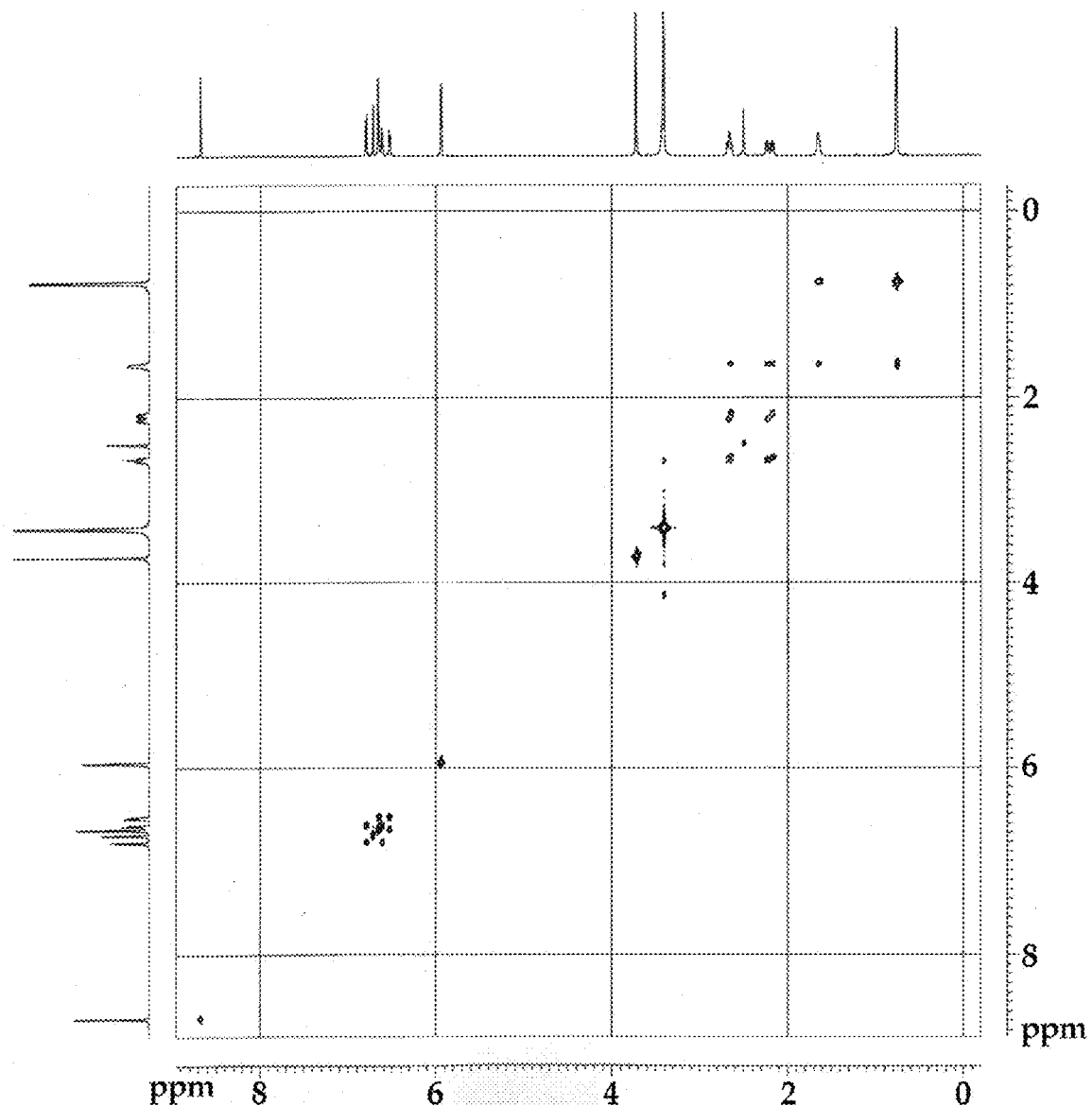
FIG. 4 shows the $^1$H-$^1$H COSY spectrum of the inventive lignan compound.
Figure 5:
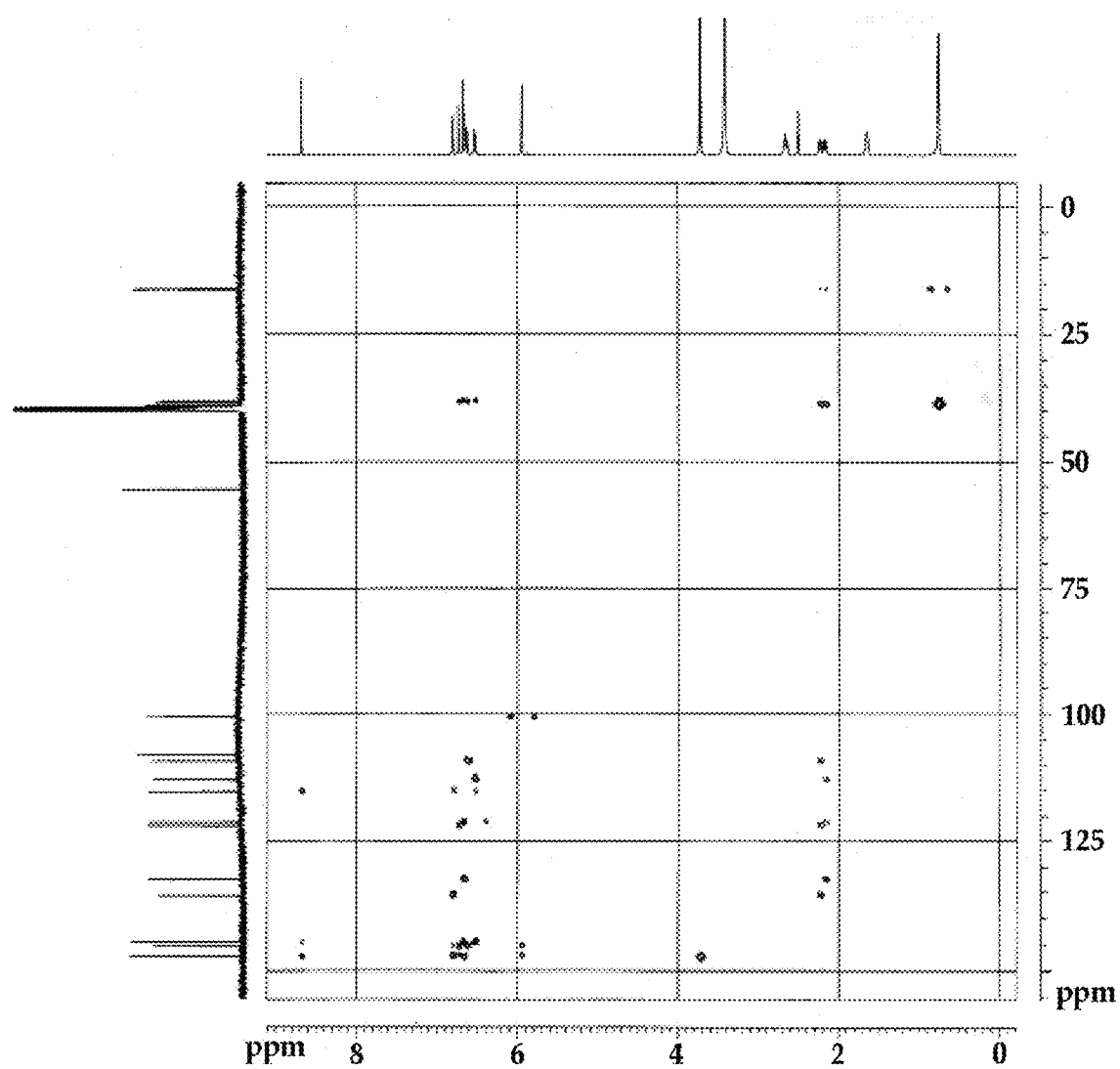
FIG. 5 shows the $^1$H-$^{13}$C HMBC spectrum of the inventive lignan compound.

To determine the structure of the isolated single material fraction III-B-2, the $^1$H-NMR spectrum and $^{13}$C-NMR spectrum were analyzed at 600 MHz and 150 MHz, respectively, in DMSO solvent. The results were shown in FIGS. 2 and 3, respectively. To determine $^1$H-$^1$H correlation and $^1$H-$^{13}$C correlation on the basis of the results of the $^{13}$C-NMR and $^1$H-NMR spectrum analyses, the $^1$H-$^1$H COSY spectrum and $^1$H-$^{13}$C HMBC spectrum were analyzed. The results were shown in FIGS. 4 and 5, respectively. The results of the $^1$H-NMR, $^{13}$C-NMR, $^1$H-$^1$H COSY and $^1$H-$^{13}$C HMBC spectrum analyses were collectively analyzed and the results were shown in Table 1 below.

TABLE 1

| Position | $^{13}$C-NMR | $^1$H-NMR | $^1$H-$^1$H COSY | $^1$H-$^{13}$C HMBC |
|---|---|---|---|---|
| 1 | 135.4 | | | |
| 2 | 109.2 | 6.72 brs | | C-7, C-6, C-4, C-3 |
| 3 | 147.3 | | | |
| 4 | 145.1 | | | |
| 5 | 107.9 | 6.79 d (7.8) | 6.61 | C-6, C-4, C-3, C-1 |
| 6 | 121.7 | 6.61 dd (7.8) | 6.79 | C-7, C-5, C-4, C-2, C-1 |
| 7 | 38.2 | 2.23 dd (13.2, 9.3) | 1.64, 2.66 | C-8, C-6, C-2, C-1 |
| | | 2.66 dd (13.2, 4.8) | 1.64, 2.23 | C-9, C-8, C-6, C-2, C-1 |
| 8 | 38.7 | 1.64 brs | 0.75, 2.23, 2.66 | C-7 |
| 9 | 16.0 | 0.75 d (6.3) | 1.64 | C-8, C-7 |
| 1' | 132.4 | | | |
| 2' | 112.9 | 6.66 brs | | C-7', C-6', C-4', C-3' |
| 3' | 147.1 | | | |
| 4' | 144.4 | | | |
| 5' | 115.2 | 6.66 d (7.9) | 6.53 | C-6', C-4', C-3', C-1' |
| 6' | 121.0 | 6.53 d (7.9, 1.1) | 6.66 | C-7', C-5', C-4', C-2', C-1' |
| 7' | 38.0 | 2.17 dd (13.2, 9.3) | 1.64, 2.66 | C-8', C-6', C-2', C-1' |
| | | 2.66 dd (13.2, 4.8) | 1.64, 2.17 | C-9', C-8', C-6', C-2', C-1' |
| 8' | 38.7 | 1.64 brs | 0.75, 2.17, 2.66 | C-7' |
| 9' | 16.1 | 0.75 d (6.3) | 1.64 | C-8', C-7' |
| OMe | 55.5 | 3.72 (s) | | |
| O—CH$_2$—O | 100.6 | 5.95 d (4.8) | | C-3, C-4 |

<1-3> Mass Analysis

Figure 6:
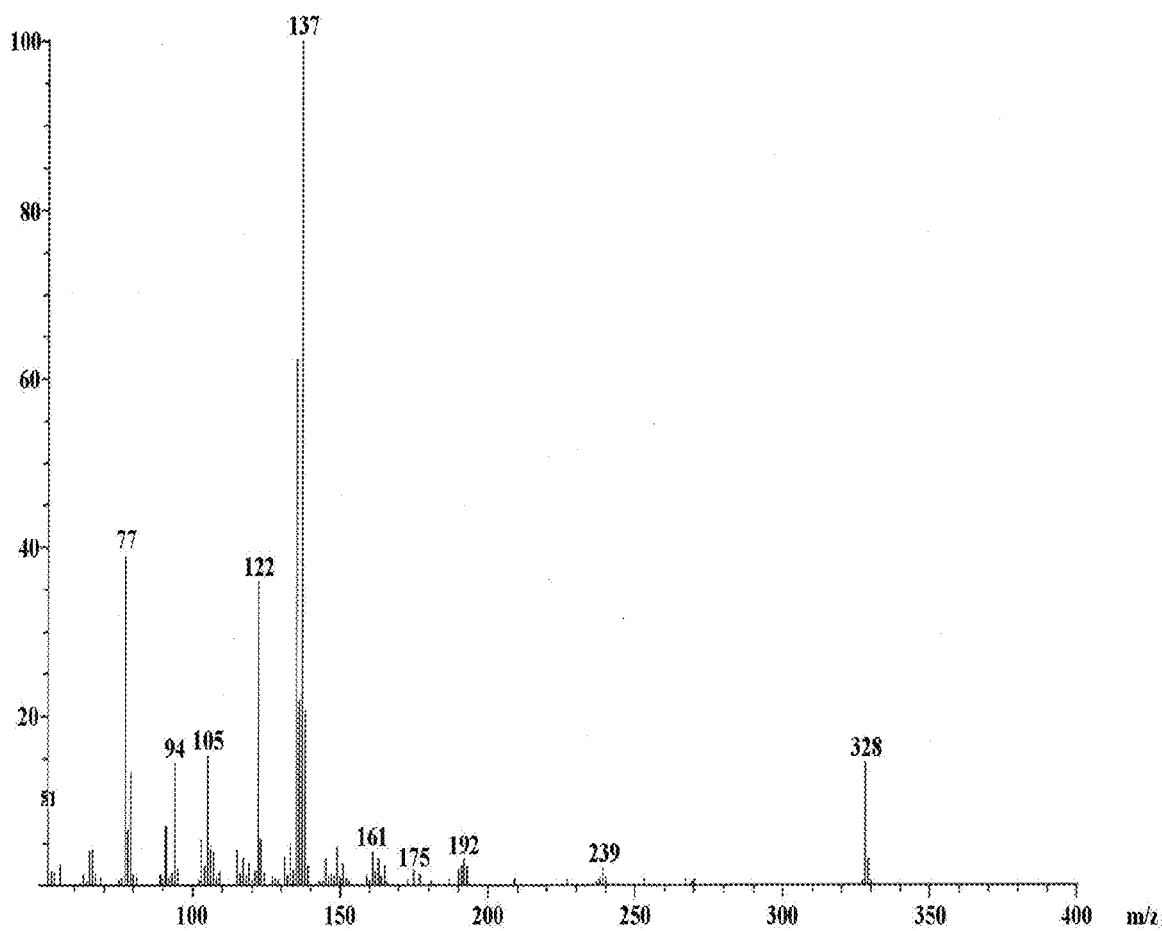
FIG. 6 shows the E1-Mass spectrum of the inventive lignan compound.

The results of EI/MS conducted to analyze the mass of the above-isolated single material were shown in FIG. 6. In the EI/MS analysis, [M]$^+$ was observed at m/z 328, indicating that the isolated compound has a molecular weight of 328 and a molecular formula of $C_{20}H_{24}O_4$.

The results of the $^1$H-NMR, $^{13}$C-NMR, $^1$H-$^1$H COSY, $^1$H-$^{13}$C HMBC and EI/MS spectrum analyses were analyzed comparatively with the previously reported study results (Woo, W. S. et al., *Phytochemistry*, 26: 1542-1543, 1987). As a result, it was found that the isolated single material was macelignan represented by Chemical Formula I:

[Chemical Formula 1]

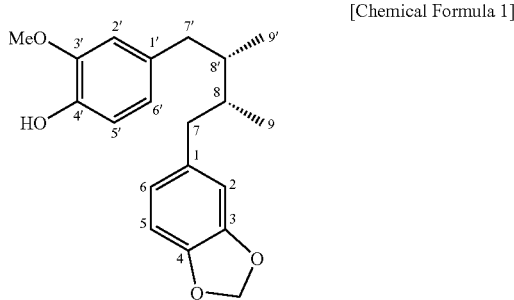 [SMILES: COc1cc(C[C@H](C)[C@H](C)Cc2ccc3c(c2)OCO3)ccc1O]

Example 2

Examination of Cytotoxicity Effect of Inventive Lignan Compound

<2-1> Culture of RAW264.7 Cell Line

In order to examine the effect of macelignan obtained in <Example 1> on the production of inflammatory response mediators, the macrophage RAW264.7 cell line was used. The macrophage RAW264.7 cell line (ATCC TIB-71) was purchased from American Tissue Culture Collection (Rockville, Md., USA). The cell line was cultured in DMEM (Dulbecco's Modified Eagle's Medium, Gibco, USA) supplemented with 10% heat inactivated FBS (fetal bovine serum, Gibco, USA), 100 U/ml penicillin G and 100 μg/ml streptomycin, in a 5% CO$_2$ incubator at 37° C.

<2-2> Measurement of Cytotoxicity

In order to examine the effect of the inventive macelignan on the viability of RAW 264.7 cells, analysis was performed based on the reduction of MTT changed into a purple formazan product by mitochondrial dehydrogenase (Hayon T. et al., *Leuk. Lymphoma.* 44(11): 1957-1962, 2003). 1×10$^6$ cells/ml of RAW264.7 cells were inoculated into RPMI 1640 medium, and after 6 hours, were treated with the inventive macelignan at concentrations up to 1-80 μM/ml. After 24 hours, the viability of the cells was measured by the MTT assay.

Figure 7:
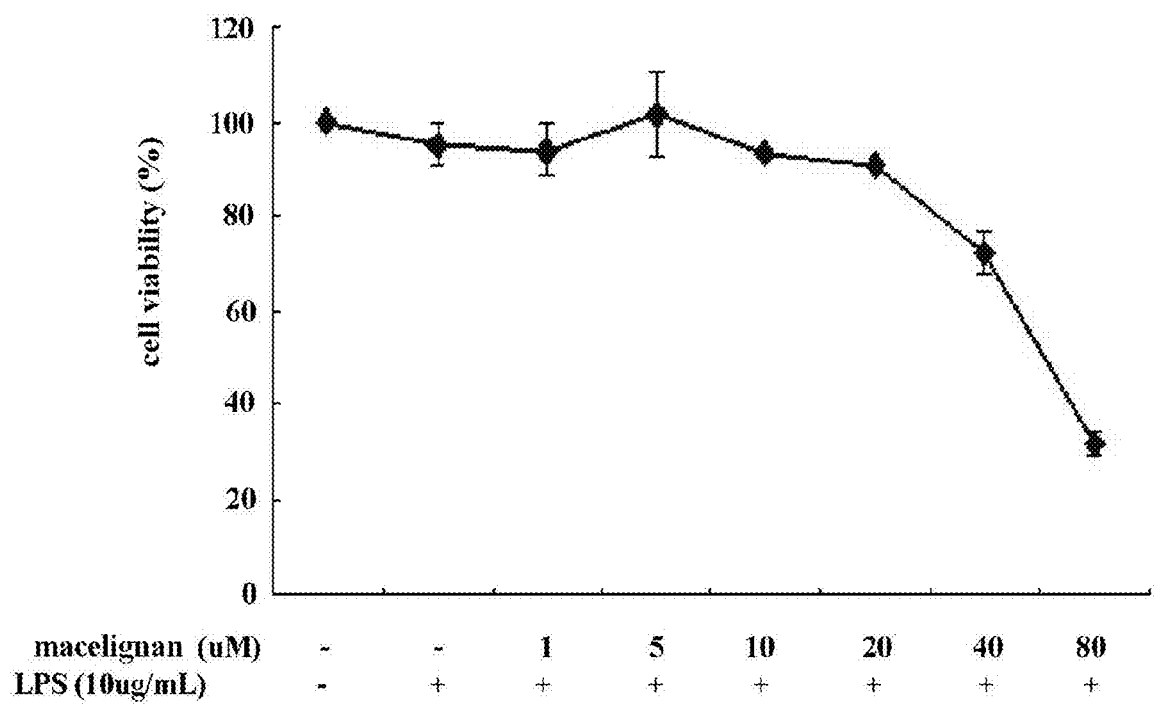
FIG. 7 shows the cytotoxicity effect of the inventive lignan compound.

As a result, as shown in FIG. 7, the inventive macelignan had no significant effect on the viability of the RAW264.7 cells at macelignan concentrations of 1-20 μM. Based on these results, 1-20 μM concentrations of macelignan were used in a subsequent inflammation test.

Example 3

Examination of NO-Inhibitory Effect of Inventive Lignan Compound

<3-1> Inhibition of NO Production

Macrophages stimulated by IFN-γ or LPS highly express iNOS to produce a large amount of inflammatory response mediator NO (Miyasaka and Hirata., *Immunol. Today.*, 16: 128-130, 1995; Guzik et al., *J. Physiol. Pharmacol.*, 54(4):

469-487, 2003). Accordingly, whether the inventive macelignan has any effect on NO production in RAW264.7 cells activated with LPS was examined.

RAW264.7 cells were diluted at a concentration of $1\times10^6$ cell/ml and then inoculated into RPMI 1640 medium. After 5 hours, the inventive macelignan was added to the medium at each of a concentration of 1-20 μM, followed by incubation for 2 hours. Then, the medium was treated with LPS (10 μg/ml) and incubated for 24 hours. A control group was treated only with LPS. The production of NO was quantified by measuring $NO_2^-$, a reaction product of NO, using the remains of cell culture (Han et al., *Life Sci.*, 75(6): 675-684, 2004). 100 μl of the remains of cell culture and the same volume of Greiss reagent (0.5% sulfanilyamide, 0.05% N-(1-naphthyl)ethylene diamine dihydrochloride/2.5% $H_3PO_4$) were mixed with each other on a 96-well tissue culture plate and allowed to react in a dark place for 10 minutes. Then, the absorbance of the sample was measured at 550 nm using the ELISA microplate reader. The concentration of $NO_2^-$ was plotted as a standard curve using $NaNO_3$, and the production of NO was determined comparable to the standard curve. All tests were repeated at three times, and then quantified by student's t-test.

Figure 8:
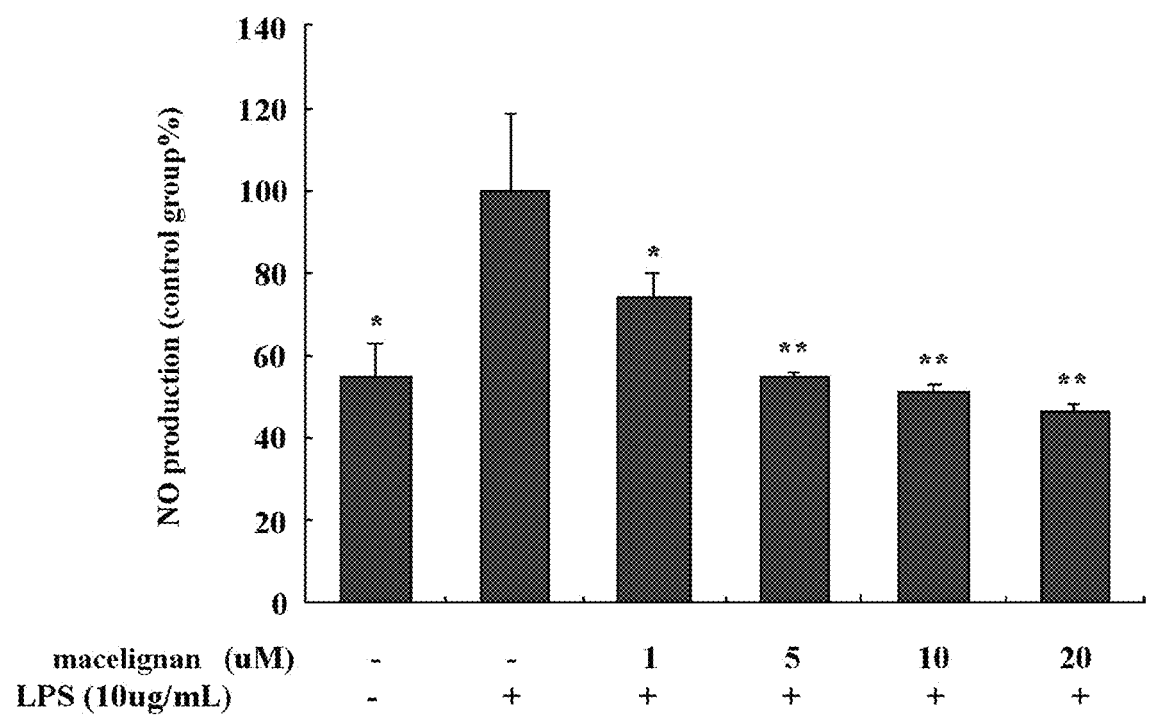
FIG. 8 shows analysis results for the NO production-inhibitory effect of the inventive lignan compound.

As a result, as shown in FIG. 8, the production of NO was greatly increased as a result of treatment with LPS alone, but it was concentration-dependently inhibited by treatment with the inventive macelignan. Particularly, it could be observed that the inventive macelignan had excellent effects on the inhibition of NO production even at low concentrations of 1 μM and 5 μM (P<0.01). Also, in the case of treatment with 20 μM of macelignan, the production of NO was inhibited to an extent almost similar to that of the group treated with nothing.

<3-2> Inhibition of iNOS Expression

If macrophages are stimulated by LPS, iNOS will be highly expressed while producing a large amount of NO. Accordingly, in order to examine the relationship between the NO producing inhibition of the inventive macelignan confirmed in Example <3-1> and the iNOS, the effect of the macelignan on the expression of iNOS was measured.

For this purpose, RAW 264.7 cells treated with the inventive macelignan and LPS were dissolved and the protein was quantified by the Bradford assay. 10 μg of the protein was separated on 10% SDS-PAGE, and then transferred to a nitrocellulose membrane by a transfer solution (20% methanol, 25 mM Tris, 192 mM glycine, pH 8.3) (Hall, Methods Mol. Biol., 261: 167-174, 2004). The nitrocellulose membrane was brought into close contact with SDS-polyacrylamide gel, and then placed in a mini-gel transfer kit. Then, the sample was loaded into the kit and electrophoresed at 100 V for 1 hour. Next, the membrane was washed one time with TBST (Tris buffered saline Tween-20) solution and dried on dry filter paper at room temperature. To eliminate non-specific reactions, the membrane was left to stand while sufficiently shaking it with 5% containing non-fat skim milk in TBST solution at 4° C. for at least 24 hours. Then, the membrane was washed three times with TBST solution and injected with an anti-iNOS antibody (1:2,000) (Calbiochem) and allowed to react at room temperature for 1 hour. Then, the membrane was washed three times with TBST solution for 10 minutes each washing time. The washed membrane was injected with anti-rabbit IgG-HRP conjugated with HRP (horse radish peroxidase) (1:2,000) (Calbiochem) and allowed to react on a shaker for 1 hour. Then, the membrane was washed three times with TBST solution, after which it was immersed in ECL (enhanced chemiluminescence) solution and evenly wetted with the solution while shaking it for 1 minute. The ECL solution was prepared by mixing solution A (containing luminol and enhancer) with solution B (containing hydrogen peroxide) in the same amount and shaking the mixed solution well for 1 minute. The membrane was taken out from the ECL solution, dehydrated and then scanned with X-ray films in a dark room.

Figure 9:
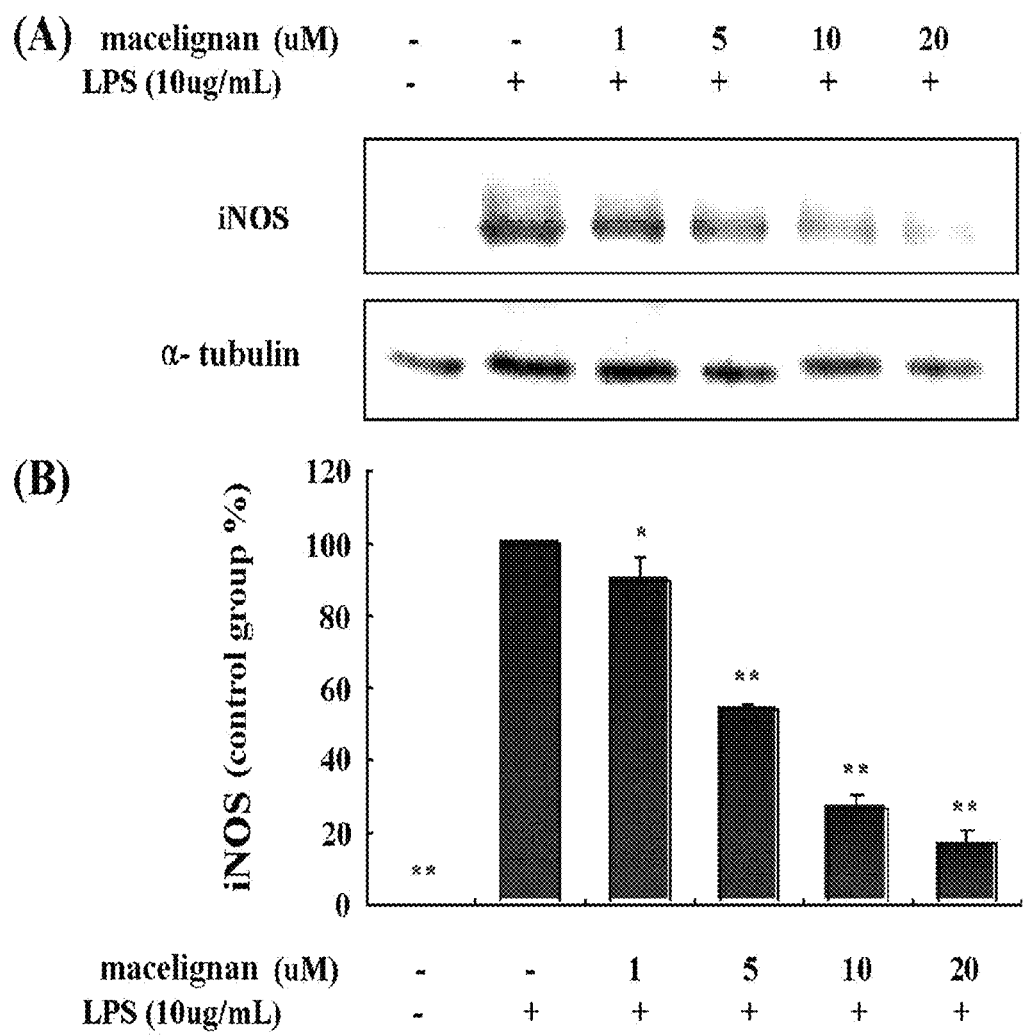
FIG. 9 shows analysis results for the iNOS expression-inhibitory effect of the inventive lignan compound.
A: Western blot analysis result
B: graph showing iNOS protein levels relative to a control group stimulated by LPS

As a result, as shown in FIG. 9, the inventive macelignan concentration-dependently inhibited the expression of iNOS in macrophages and showed a remarkable inhibitory effect starting with a concentration of 5 μM (P<0.01).

From the above results, it could be found that the inventive macelignan not only inhibits the production of inflammation-inducing factor NO, but also inhibits the expression of iNOS that produces NO.

Example 4

Examination of COX-2-Inhibitory Effect of Inventive Lignan Compound

<4-1> Inhibition of PEG2 Production

Similarly to the fact that iNOS has a close connection with inflammation reactions, it is known that COX-2 is an enzyme necessary for the production of prostaglandins (PG) mediating inflammatory reactions, and the expressions and activities of iNOS and COX have a connection with each other (Surh et al., *Mutat. Res.*, 481: 243-268, 2001). Accordingly, whether the inventive macelignan has any effect on the production of $PGE_2$ in macrophages activated by LPS was examined.

First, $1\times10^6$ cells/ml of RAW264.7 cells were inoculated into a 96-well tissue culture plate and left to stand at room temperature for 5 hours. Then, the inventive macelignan was added to the cells at each of concentrations of 1-20 μM and incubated for 2 hours. A negative control group was not treated with anything, and a positive control group was treated with curcumin (isolated from *Curcuma longa*; Sigma) reported to have $PGE_2$ inhibitory activity. Then, the cells were treated with 1 μg/ml of LPS and cultured for 18 hours. The production of $PGE_2$ in the macrophages was quantified by an assay kit (R&D System Inc, Minneapolis, USA) using an ELISA method (Chen et al., *Biochem. Pharmacol.*, 68: 1089-1100, 2002).

As a result, as shown in FIG. 10, it was observed that the production of $PGE_2$ was greatly increased as a result of treatment with LPS alone, but was concentration-dependently inhibited by treatment with the inventive macelignan. This inhibitory effect was shown even at a macelignan concentration of 5 μM. This $PGE_2$ production-inhibitory effect of the inventive macelignan was almost similar to the case of treatment with curcumin, and showed the same pattern as the NO and iNOS inhibitory effect confirmed in <Example 3> (P<0.05).

<4-2> Inhibition of COX-2 Expression

The present inventors examined the expression of COX-2 having a direct effect on the production of $PGE_2$ by Western blot analysis. It was performed in the same manner as described in Example <3-2>, except that an anti-COX-2 antibody (1:2,000) (Calbiochem) was used as a primary antibody, and anti-goat IgG-HRP (1:2,000) (Calbiochem) was used as a secondary antibody.

Figure 11:
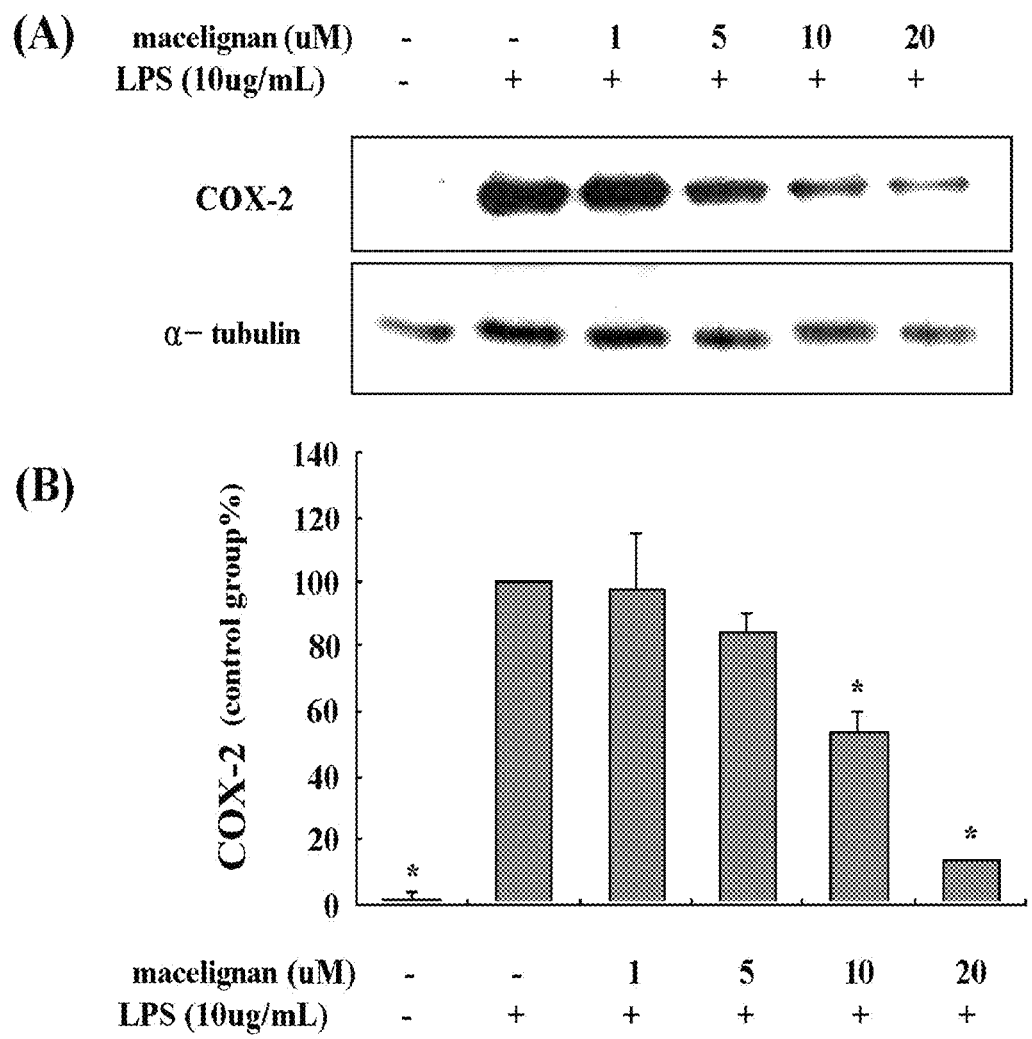
FIG. 11 shows analysis results for the COX-2 expression-inhibitory effect of the inventive lignan compound.
A: Western blot analysis result
B: graph showing COX-2 protein levels relative to a control group stimulated by LPS

As a result, as shown in FIG. 11, the inventive macelignan inhibited the expression of the COX-2 protein in a concentration-dependent manner. Particularly at macelignan concentrations of 10-20 μM, the expression level of the COX-2 protein was significantly reduced.

From the above results, it could be found that the inventive macelignan not only inhibits the production of inflammation-inducing factor $PEG_2$, but also inhibits the expression of COX-2 that produces $PEG_2$.

Example 5

Examination of TNF-α Inhibitory Effect of Inventive Lignan Compound

TNF-α is an inflammatory cytokine which plays an important role in inflammatory reactions. Accordingly, the effect of the inventive macelignan on the production of TNF-α was examined.

<5-1> Inhibition of TNF-α Production in Macrophages

First, $1 \times 10^6$ cell/ml of RAW264.7 cells were inoculated into a 96-well tissue culture plate and left to stand at room temperature for 5 hours. Then, the inventive macelignan was added to the cells at each of a concentration of 1-20 μM and incubated for 2 hours. A negative control group was not treated with anything, and a positive control group was treated with curcumin (Sigma) (Araujo and Leon, *Mem. Inst. Oswaldo. Cruz.*, 96(5): 723-728, 2001; Chainani-Wu, J. *Altern. Complement.*, 9(1): 161-168, 2003). Then, the cells were treated with 1 μg/ml of LPS and cultured for 18 hours. The production of TNF-α in the macrophages was quantified with an assay kit (R&D System Inc, Minneapolis, USA) using an ELISA method (Chen et al., *J. Dermatol. Sci.* 29: 97-103, 2002).

As a result, as shown in FIG. 12, the production of TNF-α was significantly reduced starting with a macelignan treatment concentration of 5 μM ($P<0.05$).

<5-2> Inhibition of TNF-α Production in Human Monocytic Cells

By the present inventors, the production of TNF-α in human monocytic U937 cells activated with *Propionibacterium acnes* was measured in the same manner as in Example <5-1>. However, a positive control group was treated with indomethacin (Sigma) (Walch and Morris, *Endocrinology.* 143(9): 3276-3283, 2002).

As a result, as shown in FIG. 13, it could be observed that the production of TNF-α in the human monocytic cells was reduced by the inventive macelignan in a concentration-dependent manner ($P<0.01$).

From the above results, it could be seen that the inventive macelignan inhibited the production of TNF-α that induced and/or mediated acute inflammation and systemic inflammatory reactions.

Example 6

Examination of Anti-Inflammatory Activity of Inventive Lignan Compound in Animal Model The anti-inflammatory activity of the lignan compound isolated and purified in <Example 1> was tested in animal models. The anti-inflammatory activity was measured by edema inhibition test on rats. As the test animals, 5-week-old Wistar rats (DaeHan Biolink Co., Ltd, Korea) were used. The animals were provided with standard pellet forming rat feed (Cheiljedang Corporation, Korea) and given freely to feed and water. Also, the animals were housed in conditions of 12-hr light/12-hr dark cycle, temperature of 25±2° C. and humidity of 60±10%. Inflammation inducing agent TPA (12-O-tetradecanoylphorbol-13-acetate; Sigma) was dissolved in acetone to a concentration of 200 μg/mL. The edemas of the rat ears were induced by applying the TPA solution locally to each of the outer and inner faces of the ear in an amount of 10 μl/ear (4 μg/ear). The macelignan purified in <Example 1> and non-steroidal anti-inflammatory drug indomethacin as a control substance were dissolved in acetone and used in amounts of 20, 200 and 2000 μg/ear. Each of the macelignan and the indomethacin was applied locally to the rat ears at 30 minutes after treatment with TPA. A control group was locally applied with acetone. The thickness of the rat ears was measured with a caliper 8 hours after treatment with each of the substances. An increase in the ear thickness in the group treated with the sample was compared to that of the group untreated with the sample, and inflammation inhibitory effect was measured by calculating percent edema inhibition. The results were shown in Table 2 below.

TABLE 2

| Drug administered | Number of rats | Dose (μg/ear) | Edema thickness (μm) | Edema inhibition (%) |
|---|---|---|---|---|
| Control | 20 | 0 | 248 ± 8 | |
| Inventive macelignan | 20 | 20 | 157 ± 9* | 36.7 |
| | 20 | 200 | 98 ± 6* | 60.5 |
| | 20 | 2000 | 52 ± 4* | 79.0 |
| indomethacin | 20 | 20 | 185 ± 5* | 25.0 |
| | 20 | 200 | 108 ± 8* | 56.5 |
| | 20 | 2000 | 64 ± 7* | 74.2 |

*$p < 0.01$

Example 7

Preparation of Macelignan-Comprising Creams and Examination of Anti-Inflammatory Activities Thereof <7-1> Preparation of Creams Comprising Macelignan Using the inventive macelignan, each of creams having various compositions shown in Table 3 below was prepared. First, substances indicated as "B" in Table 3 were dissolved at 75-80° C. Also, among substances indicated as "C" in Table 3, cetyl alcohol and a preservative were dissolved at the same temperature as above. The substances indicated as "C" were emulsified in the substances indicated as "B". Then, the inventive macelignan indicated as "A" in Table 3 was added to the emulsions at each of concentrations of 5.0, 0.5, 0.05 and 0.005%. Finally, a fragrance was added and the balance of purified water was then added, thus preparing creams.

TABLE 3

| | | 1 | 2 | 3 | 4 |
|---|---|---|---|---|---|
| Main components | A | 5.0% macelignan | 0.5% macelignan | 0.05% macelignan | 0.005% macelignan |
| | B | 2.0% glycerin<br>2.0% propylene glycol<br>8.0% chloride lauryl sulfide<br>5.4% stearin<br>4.5% mineral oil | 2.0% glycerin<br>2.0% propylene glycol<br>8.0% chloride lauryl sulfide<br>5.4% stearin<br>4.5% mineral oil | 2.0% glycerin<br>2.0% propylene glycol<br>8.0% chloride lauryl sulfide<br>5.4% stearin<br>4.5% mineral oil | 2.0% glycerin<br>2.0% propylene glycol<br>8.0% chloride lauryl sulfide<br>5.4% stearin<br>4.5% mineral oil |

TABLE 3-continued

| | 1 | 2 | 3 | 4 |
|---|---|---|---|---|
| C | 0.02% fragrance 6.5% cetyl alcohol Balance purified water 0.1% preservative | 0.02% fragrance 6.5% cetyl alcohol Balance purified water 0.1% preservative | 0.02% fragrance 6.5% cetyl alcohol Balance purified water 0.1% preservative | 0.02% fragrance 6.5% cetyl alcohol Balance purified water 0.1% preservative |

<7-2> Examination of Anti-Inflammatory Activity

The anti-inflammatory activities of the macelignan-comprising creams prepared in Example <7-1> were measured through edema inhibition test on rats. The edema inhibition test was performed in the same manner as in <Example 6>. The results were shown in Table 4 below.

TABLE 4

| | Sample | | | |
|---|---|---|---|---|
| | 1 | 2 | 3 | 4 |
| Macelignan content | 0.005% | 0.05% | 0.5% | 5% |
| Edema inhibition (%) | 14.2 | 42.3 | 64.6 | 88.7 |

From the results in Table 4, it could be seen that the creams comprising the inventive macelignan inhibited the rat edema induced by TPA in a manner dependent on the concentration of the macelignan comprised in each of the cream.

Example 8

Examination of Anti-Inflammatory Activity of *Myristica fragrans* Extract

<8-1> Preparation of Methanol Extract

To 100 g (dry weight) of dried and crushed nutmeg, 400 ml of 95-vol % methanol was added and left to stand at room temperature for 2 days. The solution was filtered through Whatman filter paper No. 2. The filtration step was repeated two times. The methanol filtrate was concentrated under vacuum and lyophilized to obtain 16.2 g of a methanol crude extract.

<8-2> Preparation of Hexane Extract

To 100 g (dry weight) of dried and crushed nutmeg, 400 ml of 100-vol % hexane was added and left to stand at room temperature for 2 days. The solution was filtered through Whatman filter paper No. 2. The filtration step was repeated two times. The hexane filtrate was concentrated under vacuum and lyophilized to obtain 37.0 g of a hexane crude extract.

<8-3> Examination of Anti-Inflammatory Activity of *Myristica fragrans* Extract in Animal Model The anti-inflammatory activities of the *Myristica fragrans* extracts prepared in Example <8-1> and Example <8-2> were tested in animal models. The anti-inflammatory activities were measured by performing edema inhibition test on rats in the same manner as in <Example 6>. The results were shown in Table 5 below.

TABLE 5

| Drug administered | Number of rats | Dose (µg/ear) | Edema thickness (µm) | Edema inhibition (%) |
|---|---|---|---|---|
| Control | 20 | 0 | 248 ± 8 | |
| Methanol crude extract | 20 | 50 | 198 ± 3* | 20.2 |
| | 20 | 500 | 119 ± 8* | 52.0 |
| | 20 | 000 | 83 ± 10* | 66.5 |
| Hexane crude extract | 20 | 50 | 207 ± 4* | 16.5 |
| | 20 | 500 | 146 ± 9* | 41.1 |
| | 20 | 5000 | 106 ± 7* | 57.3 |

*$p < 0.01$

As shown in Table 5, it could be observed that the inventive methanol crude extract and hexane crude extract of *Myristica fragrans* all inhibited the rat edema induced by TPA in a concentration-dependent manner (statistical significance $p<0.01$).

Example 9

Examination of Macelignan's Effect of Preventing or Treating Inflammatory Disease In order to investigate how macelignan directly affects T cells, the cells were stimulated and treated with macelignan at the same time. Wild type and OT-II transgenic mouse CD4 T cells, and antigen presenting cells were used (T cell receptor of CD4 T cells of OT-II transgenic mouse cells is specific for OVA peptide$_{323-339}$). Wild type CD4 T cells were stimulated with anti-CD3 and anti-CD28 antibodies (BD Pharmigen, San Diego, Calif.), and OT-II transgenic CD4 T cells were stimulated with OVA peptide (Baylor College of Medicine Protein Co-facility). The effect of macelignan was determined by the degree of proliferation of the T cells by MTT assay and by the level of cytokine production. After culturing for 4 days, the level of cytokine production was measured from the supernatant by ELISA. MTT assay was performed using cell proliferation assay kit I (Roche). Cytokines IL-4, IL-17 and IFN-g were detected. ELISA was performed using primary antibody, secondary antibody, streptavidin-alkaline phosphatase (BD Pharmigen) and phosphatase substrate (Sigma-Aldrich, St. Louis, Mo.) according to the manufacturer's instructions. Test groups are given in Table 6.

TABLE 6

| (—) | No treatment (only APC & T cell co-culture) |
|---|---|
| Ab | CD3 & CD28 antibody (stimuli to WT T cell) |
| OVA$_{323-339}$ | (stimuli to OT-II T cell) |
| 100, 10, 1, 0.1, 0.01 | Macelignan concentration (µg/ml) treated with stimulation |
| Vehicle | DMSO (Dimethyl sulfoxide) |
| APC | Antigen presenting cell only (No T cell) |

Figure 14:
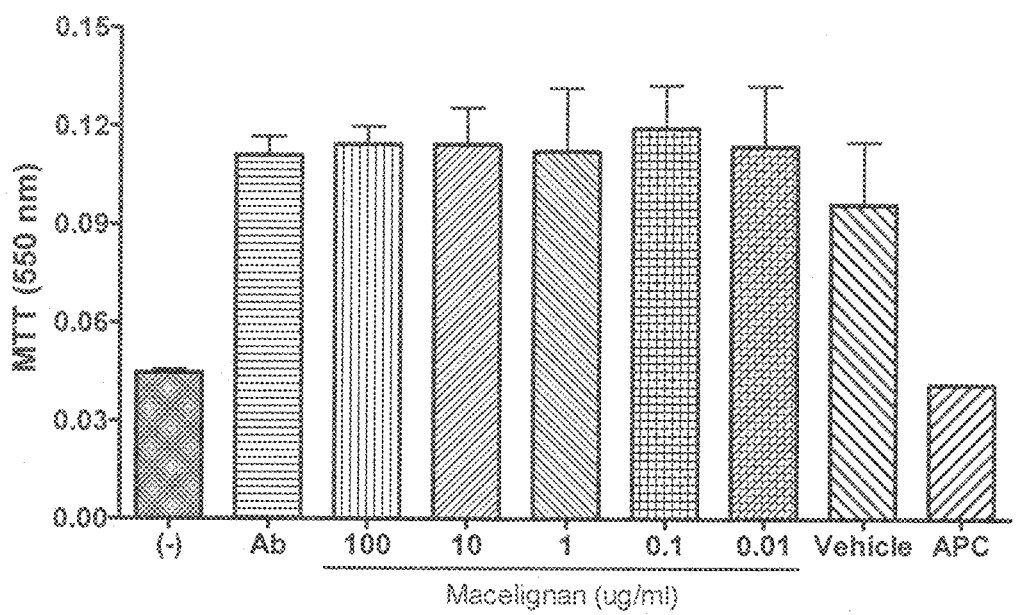
FIG. 14 shows the effect of macelignan on T cell proliferation.

As seen in FIG. 14, the group treated with antibody (Ab stimulation) showed active proliferation of T cells as compared to the negative control group. Macelignan or the vehicle had no effect on the proliferation of T cells.

Figure 15:
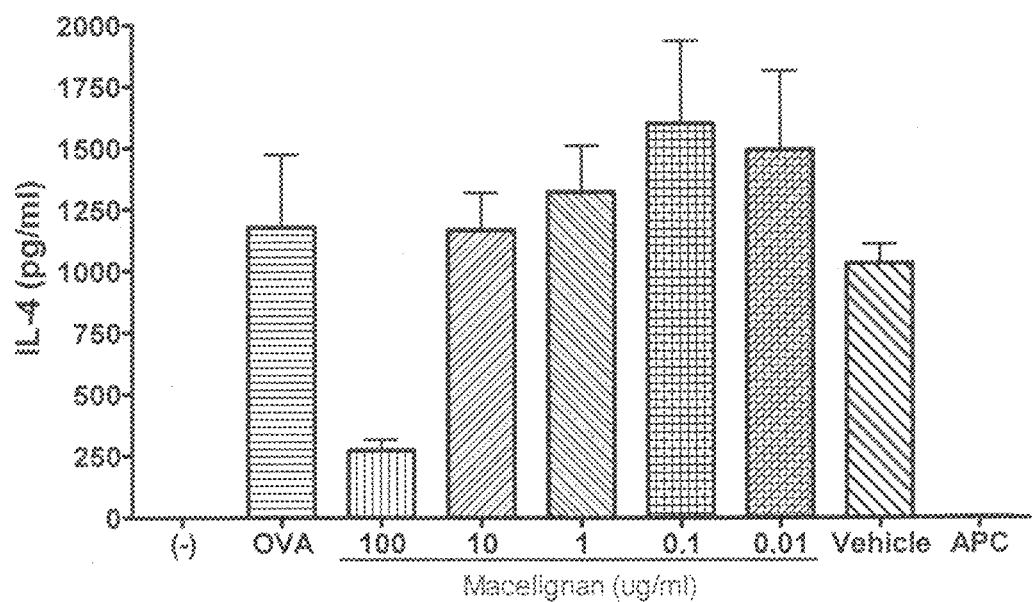
FIG. 15 shows the effect of macelignan on IL-4 production.

The effect of macelignan on IL-4 production is shown in FIG. 15. The group treated with ovalbumin peptide (OVA peptide stimulation) showed increased IL-4 production as compared to the negative control group. When macelignan was treated with high concentration (100 μg/mL), IL-4 production of OT-II T cells decreased remarkably. This suggests that macelignan may be helpful in atopic dermatitis or asthma where IL-4 plays an important role.

Figure 16:
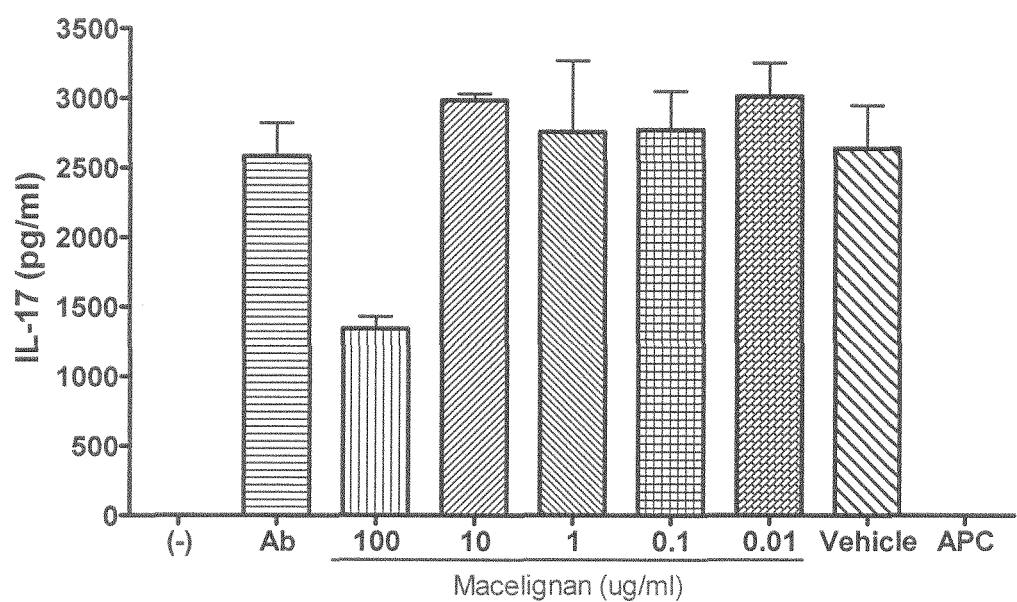
FIG. 16 shows the effect of macelignan on IL-17 production.

The effect of macelignan on IL-4 production is shown in FIG. 16. The group stimulated with antibody showed increased IL-17 production as compared to the negative control group. When macelignan was treated with high concentration (100 μg/ml), IL-17 production of T cells decreased remarkably. This suggests that macelignan may be helpful in rheumatoid arthritis where IL-17 plays an important role.

Figure 17:
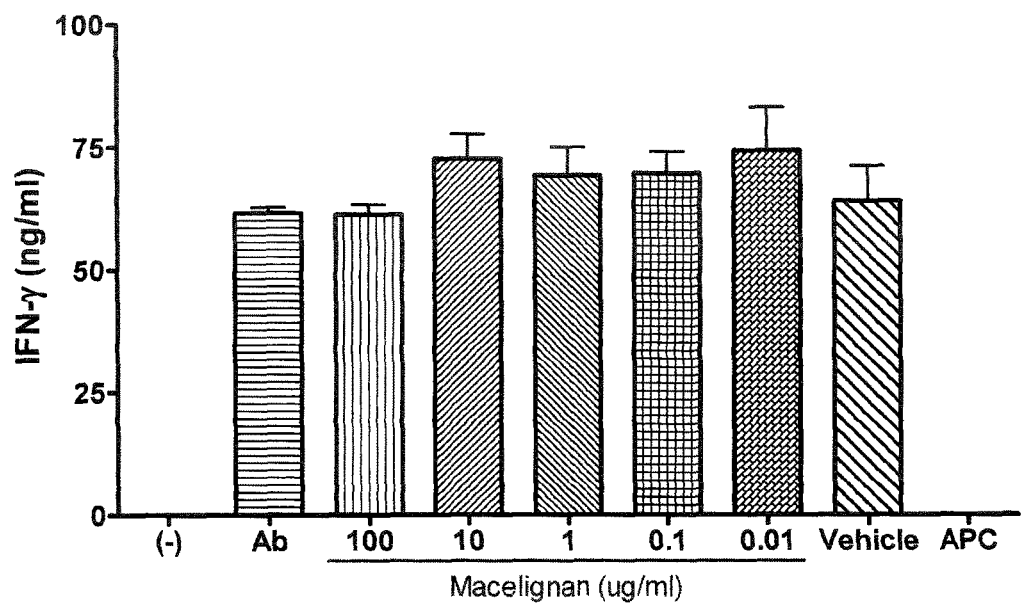
FIG. 17 shows the effect of macelignan on IFN-γ production.

The effect of macelignan on IFN-γ production is shown in FIG. 17. The group stimulated with antibody showed increased IFN-γ production as compared to the negative control group. Macelignan or the vehicle had no effect on IFN-γ production of T cells. This suggests that macelignan is not likely to induce opportunistic infection due to decreased activity of overall T cells.

Example 10

Preventing or Treating Effect of Macelignan on Atopic Dermatitis

<10-1> Test Animals

Female 8-week-old SPF (specific pathogen-free) NC/Nga mice (20-25 g) were purchased from Chungang Lab. Animal. The animals were given solid feed (Cargill Agri Purina, Korea) and water sufficiently until the test day. They were accustomed for a week at temperature 22±2° C., humidity 55±15%, with 12-hour light-dark cycle before testing.

<10-2> Preparation of Cream for Skin Application

Cream was prepared by heating stearyl alcohol, white vaselin and macelignan (or nutmeg extract) in a beaker in a bath at 75° C. In another beaker, Tween 80, propylene glycol and purified water were heated in a bath. The two mixtures were mixed homogeneously using a homomixer and then cooled. Compositions are given in Table 7.

TABLE 7

| Praparation | Low (%) | High (%) |
| --- | --- | --- |
| Stearyl alcohol | 20 | 20 |
| White vaselin | 10 | 10 |
| Tween 80 | 3.5 | 3.5 |
| Propylene glycol | 10 | 10 |
| Distilled water | 56 | 55 |
| Macelignan/Nutmeg | 0.5 | 1.5 |
| Total | 100 | 100 |

A single application dosage was 100 mg. Creams were prepared in low-concentration (20 mg/kg/day) or high-concentration (60 mg/kg/day) of macelignan or nutmeg extract.

<10-3> Preparation of Oral Administration Sample

Tween 80 was mixed with nutmeg extract (extracted with 75% methanol) or macelignan, with an amount of 1.5 times the sample weight. A single oral administration dosage was 300 μL. Samples were prepared by adding physiological saline in low-concentration (50 mg/kg) or high-concentration (150 mg/kg) of macelignan or nutmeg extract.

<10-4> Inducing Atopic Dermatitis in NC/Nga Mice Using Allergen 8-week-old NC/Nga mice (20-25 g) were purchased from Chungang Lab. Animal. After adapting for 1 week, the NC/Nga mouse was anesthetized with 90% ethyl ether (Ducsan, Korea) and hair was removed from the occipital region and the back of the mouse using depilatory cream (Reckitt Benckiser, France). After allowing micro wound healing for a day, 100 mg of mite antigen cream (Biostir, Inc. Japan) comprising *Dermatophagoides farina*, which causes atopic dermatitis, as a main ingredient was evenly applied on the ear, occipital region and back, 3 times a week (for 5 weeks, from week 9 to week 13). 2 hours before application of the mite antigen cream, 4% SDS solution was applied at the same area to increase transdermal absorption of the mite antigen cream by inducing the breakdown of skin fats and cuticle layer. From week 3 following the application, IgE value was measured to quantitate the degree of atopic dermatitis. Also during the drug treatment period (week 12 to week 13), 100 mg of the mite antigen cream was applied 3 times a week to prevent spontaneous healing of the atopic dermatitis.

<10-5> Drug Treatment and Evaluation of Therapeutic Effect

In order to induce atopic dermatitis, 100 mg of mite antigen cream was applied on the ear, occipital region and back of NC/Nga mouse (9 to 11 weeks old), except for the negative control group, 3 times a week, 2 hours after the application of 4% SDS solution. Three weeks later, it was observed whether atopic dermatitis was induced by checking skin rash, erythema, cornification, or the like. Atopic dermatitis was induced in all groups except for the negative control group. For drug treatment and evaluation of therapeutic effect, mice were grouped into 12 groups, 6 oral administration groups and 6 topical application groups (each consisting of negative control group, positive control group, macelignan low conc. group, macelignan high conc. group, nutmeg extract low conc. group, and nutmeg extract high conc. group), with n=5 per cage. During the following drug treatment and evaluation period of 2 weeks (12 to 13 weeks old), the negative control groups, which had not been treated with 4% SDS solution and mite antigen cream, were treated with physiological saline (oral administration group) or base cream (topical application group) every day, and the positive control groups, which had been treated with 100 mg of mite antigen cream 2 hours after application of 4% SDS solution, 3 times every week, were treated with physiological saline (oral administration group) or base cream (topical application group). The oral administration groups were treated with 100 mg of mite antigen cream 2 hours after application of 4% SDS solution, 3 times every week, and were treated with macelignan or nutmeg extract at low concentration (50 mg/kg/day) or high concentration (150 mg/kg/day) every day. The topical application groups were treated with 100 mg of mite antigen cream 2 hours after application of 4% SDS solution, 3 times every week, and were treated with macelignan cream or nutmeg extract cream at low concentration (20 mg/kg/day) or high concentration (60 mg/kg/day) every day. Transepidermal water loss (TEWL), skin hydration and erythema index were measured one day before the end of the test. Serum was obtained by retro-orbital blood sampling. After the end of the test (14 weeks old) spleen and skin tissues from occipital region and back were sampled and stored at −70° C. ALN (axillary lymph node) was stored in DMEM containing 2% FBS (fetal bovine serum). The skin tissues were stored in 10% formalin solution.

Treatments of the test groups are summarized in Tables 8 and 9.

TABLE 8

| Oral administration | Negative control group | Positive control group | Macelignan group | Nutmeg extract group |
|---|---|---|---|---|
| 4% SDS solution (9-week-old ~13-week-old) | − | + | + | + |
| Mite antigen cream (9-week-old ~13-week-old) | − | + | + | + |
| Treatment and evaluation (12-week-old ~13-week-old) | Saline | Saline | Macelignan Low conc.(50 mg/kg/day) High conc.(150 mg/kg/day) | Nutmeg extract Low conc.(50 mg/kg/day) High conc.(150 mg/kg/day) |

TABLE 9

| Topical application | Negative control group | Positive control group | Macelignan group | Nutmeg extract group |
|---|---|---|---|---|
| 4% SDS solution (9-week-old ~13-week-old) | − | + | + | + |
| Mite antigen cream (9-week-old ~13-week-old) | − | + | + | + |
| Treatment and evaluation (12-week-old ~13-week-old) | Base cream | Base cream | Macelignan cream Low conc. (20 mg/kg/day) High conc.(60 mg/kg/day) | Nutmeg cream Low conc. (20 mg/kg/day) High conc.(60 mg/kg/day) |

<10-6> Measurement of Total IgE in Serum

IgE, which is secreted during the differentiation of B cells and induces inflammatory response, tends to exist in high level in atopic dermatitis. In order to investigate the effect of inducing and treating atopic dermatitis, IgE level was measured before sacrificing each mouse.

Blood was taken by retro-orbital blood sampling using a capillary tube (Chase Scientific Glass, Inc., USA), which was centrifuged at 13,000 rpm to obtain serum. IgE level was measured using a mouse IgE ELISA kit (Immunology Consultants Laboratory, Inc., USA).

Figure 18:
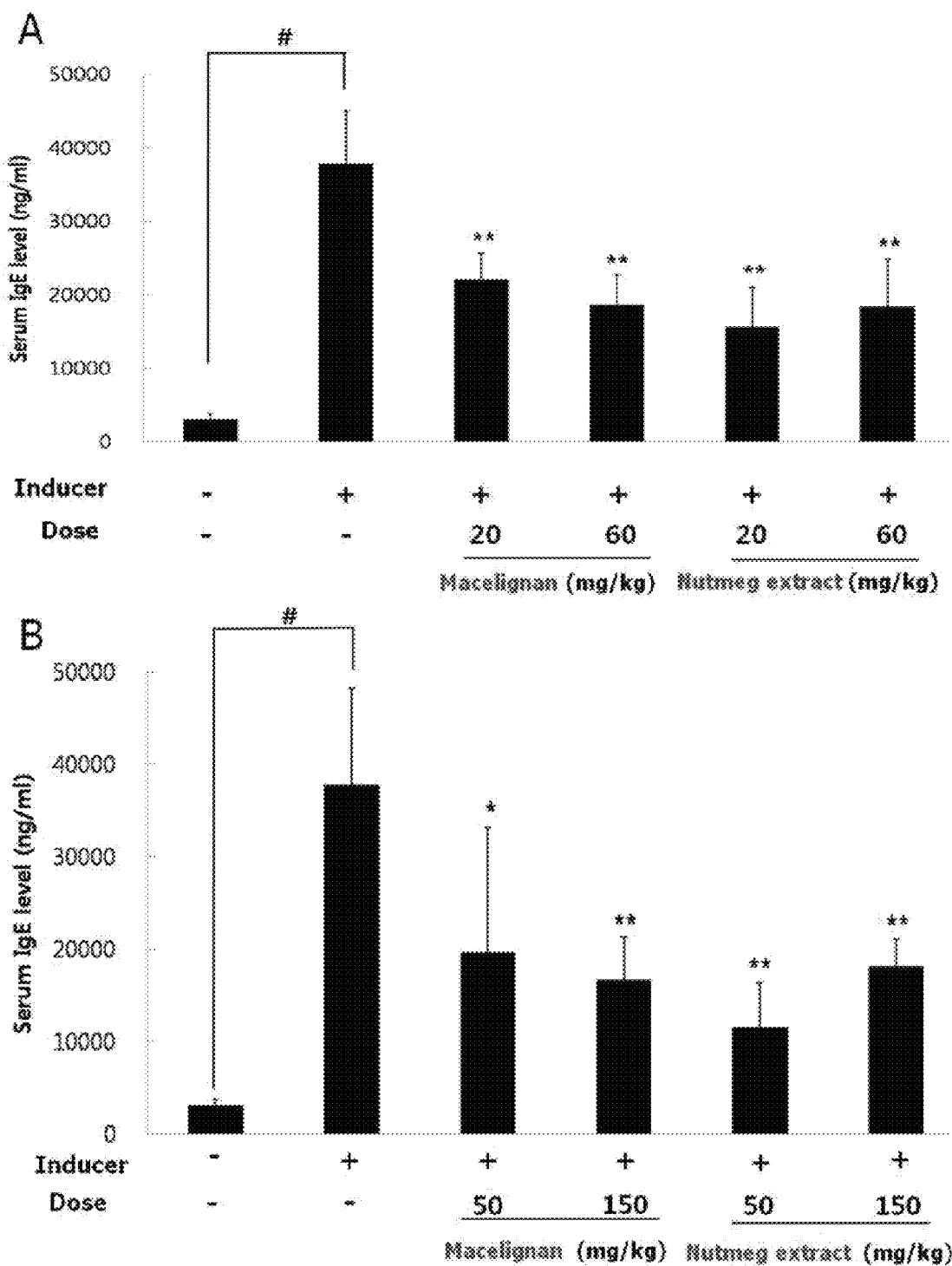
FIG. 18 shows the changes in IgE level by skin application (A) and oral administration (B) of macelignan and nutmeg extract.

As seen in FIG. 18A and Table 10, the positive control group in which the NC/Nga had been treated with mite antigen cream for 5 weeks showed remarkable increase in IgE level as compared to the negative control group. The ML-20, ML-60, NE-20 and NE-60 topical application groups showed statistically significant decrease in total IgE level as compared to the positive control group ($p<0.01$). Also, as seen in FIG. 18B and Table 11, the ML-50, ML-150, NE-50 and NE-150 oral administration groups showed statistically significant decrease in total IgE level as compared to the positive control group ($p<0.01$).

TABLE 10

Change in IgE level after topical application of macelignan and nutmeg extract

| | Control (−) | Control (+) | ML-20 | ML-60 | NE-20 | NE-60 |
|---|---|---|---|---|---|---|
| IgE (µg/ml) | 3.3 ± 0.5 | 37.8 ± 6.3 | 22.1 ± 3.6 | 18.6 ± 4.1 | 15.7 ± 5.3 | 18.8 ± 6.1 |

(ML-20: macelignan 20 mg/kg, ML-60: macelignan 60 mg/kg, NE-20: nutmeg extract 20 mg/kg, NE-60: nutmeg extract 60 mg/kg)

TABLE 11

Change in IgE level after oral administration of macelignan and nutmeg extract

|  | Control (−) | Control (+) | ML-50 | ML-150 | NE-50 | NE-150 |
| --- | --- | --- | --- | --- | --- | --- |
| IgE (µg/ml) | 2.9 ± 0.9 | 37.7 ± 9.1 | 19.6 ± 13.5 | 16.6 ± 5.3 | 11.5 ± 4.9 | 18.1 ± 2.7 |

(ML-50: macelignan 50 mg/kg, ML-150: macelignan 150 mg/kg, NE-50: nutmeg extract 50 mg/kg, NE-150: nutmeg extract 150 mg/kg)

<10-7> Skin Barrier Recovery Test

One day before the end of the experiment, TEWL, skin hydration and erythema index were measured to quantitatively compare recovery of skin barrier. TEWL was measured with a tewameter (TM300), skin hydration with a corneometer (CM825), and erythema index with a mexameter (MX18).

Figure 19:
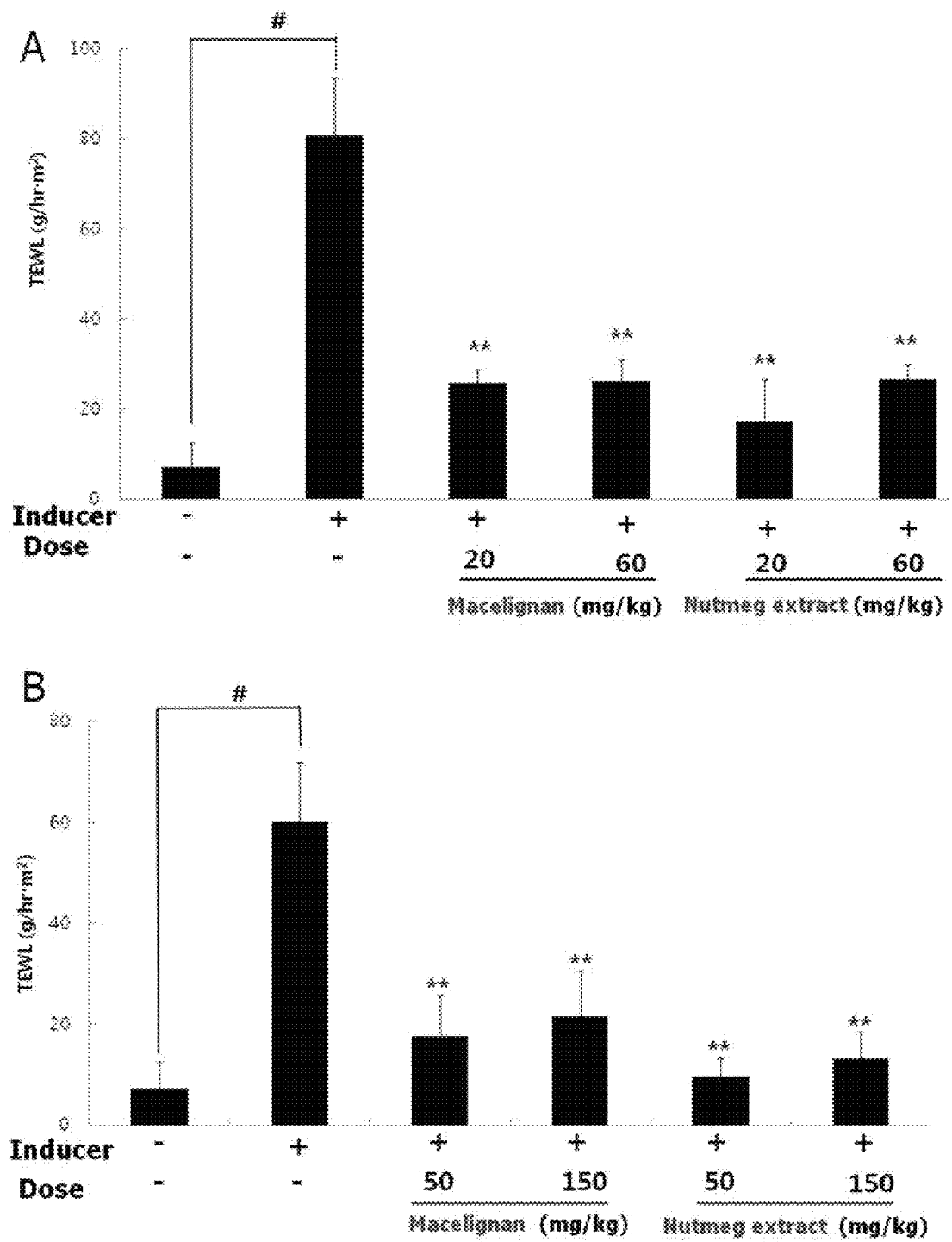
FIG. 19 shows the changes in TEWL by skin application (A) and oral administration (B) of macelignan and nutmeg extract.

The result of measuring TEWL is as seen in FIG. 19A and Table 12. The positive control group in which the NC/Nga had been treated with mite antigen cream for 5 weeks showed remarkably increased TEWL as compared to the negative control group. The ML-20, ML-60, NE-20 and NE-60 topical application groups showed statistically significant effect of suppressing TEWL as compared to the positive control group ($p<0.01$). Also, as seen in FIG. 19B and Table 13, the ML-50, ML-150, NE-50 and NE-150 oral administration groups showed statistically significant effect of suppressing TEWL as compared to the positive control group ($p<0.01$).

TABLE 12

Change in TEWL after topical application of macelignan and nutmeg extract

|  | Control (−) | Control (+) | ML-20 | ML-60 | NE-20 | NE-60 |
| --- | --- | --- | --- | --- | --- | --- |
| TEWL (g/hr · m$^2$) | 7.1 ± 5.9 | 80.5 ± 12.9 | 25.8 ± 3.1 | 26.2 ± 4.9 | 17.2 ± 9.4 | 26.7 ± 3.4 |

TABLE 13

Change in TEWL after oral administration of macelignan and nutmeg extract

|  | Control (−) | Control (+) | ML-50 | ML-150 | NE-50 | NE-150 |
| --- | --- | --- | --- | --- | --- | --- |
| TEWL (g/hr · m$^2$) | 7.3 ± 5.1 | 60.5 ± 11.7 | 17.6 ± 8.1 | 21.5 ± 9.2 | 9.7 ± 3.7 | 13.2 ± 5.6 |

Figure 20:
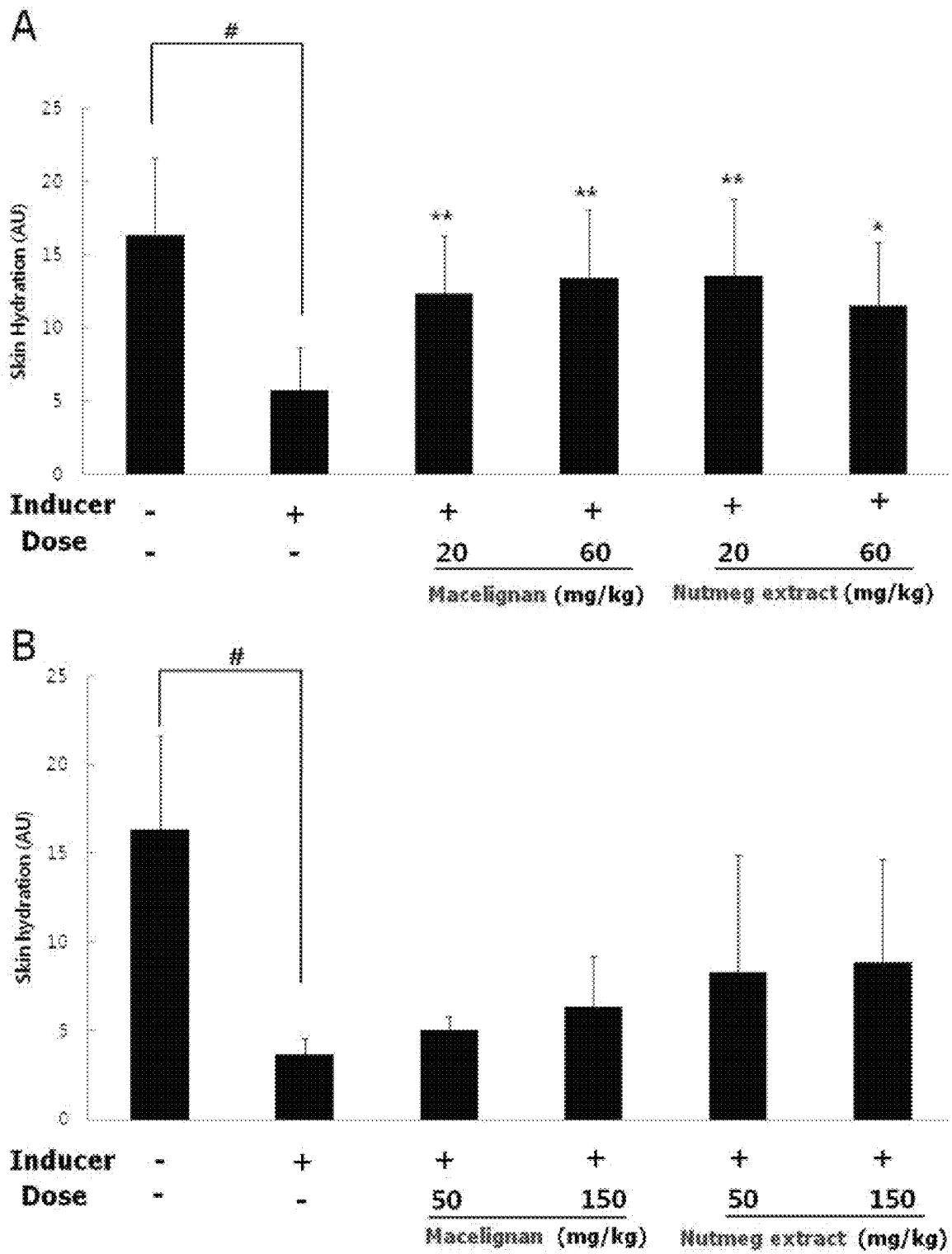
FIG. 20 shows the changes in skin hydration by skin application (A) and oral administration (B) of macelignan and nutmeg extract.

The result of measuring skin hydration is as seen in FIG. 20A and Table 14. The positive control group in which the NC/Nga had been treated with mite antigen cream for 5 weeks showed remarkably decreased skin hydration as compared to the negative control group. The ML-20, ML-60, NE-20 and NE-60 topical application groups showed statistically significant effect of increasing skin hydration as compared to the positive control group ($p<0.01$). Also, as seen in FIG. 20B and Table 15, the positive control group in which the NC/Nga had been treated with mite antigen cream for 5 weeks showed remarkably decreased skin hydration as compared to the negative control group. The ML-50, ML-150, NE-50 and NE-150 oral administration groups showed effect of increasing skin hydration as compared to the positive control group.

TABLE 14

Change in skin hydration after topical application of macelignan and nutmeg extract

|  | Control (−) | Control (+) | ML-20 | ML-60 | NE-20 | NE-60 |
|---|---|---|---|---|---|---|
| Skin Hydration (AU) | 16.3 ± 5.3 | 5.7 ± 3.0 | 12.4 ± 3.9 | 13.4 ± 4.7 | 13.6 ± 5.2 | 11.5 ± 4.3 |

TABLE 15

Change in skin hydration after oral administration of macelignan and nutmeg extract

|  | Control (−) | Control (+) | ML-50 | ML-150 | NE-50 | NE-150 |
|---|---|---|---|---|---|---|
| Skin Hydration (AU) | 16.3 ± 5.3 | 3.7 ± 0.9 | 5.0 ± 0.8 | 6.4 ± 2.8 | 8.3 ± 6.6 | 8.9 ± 5.8 |

Figure 21:
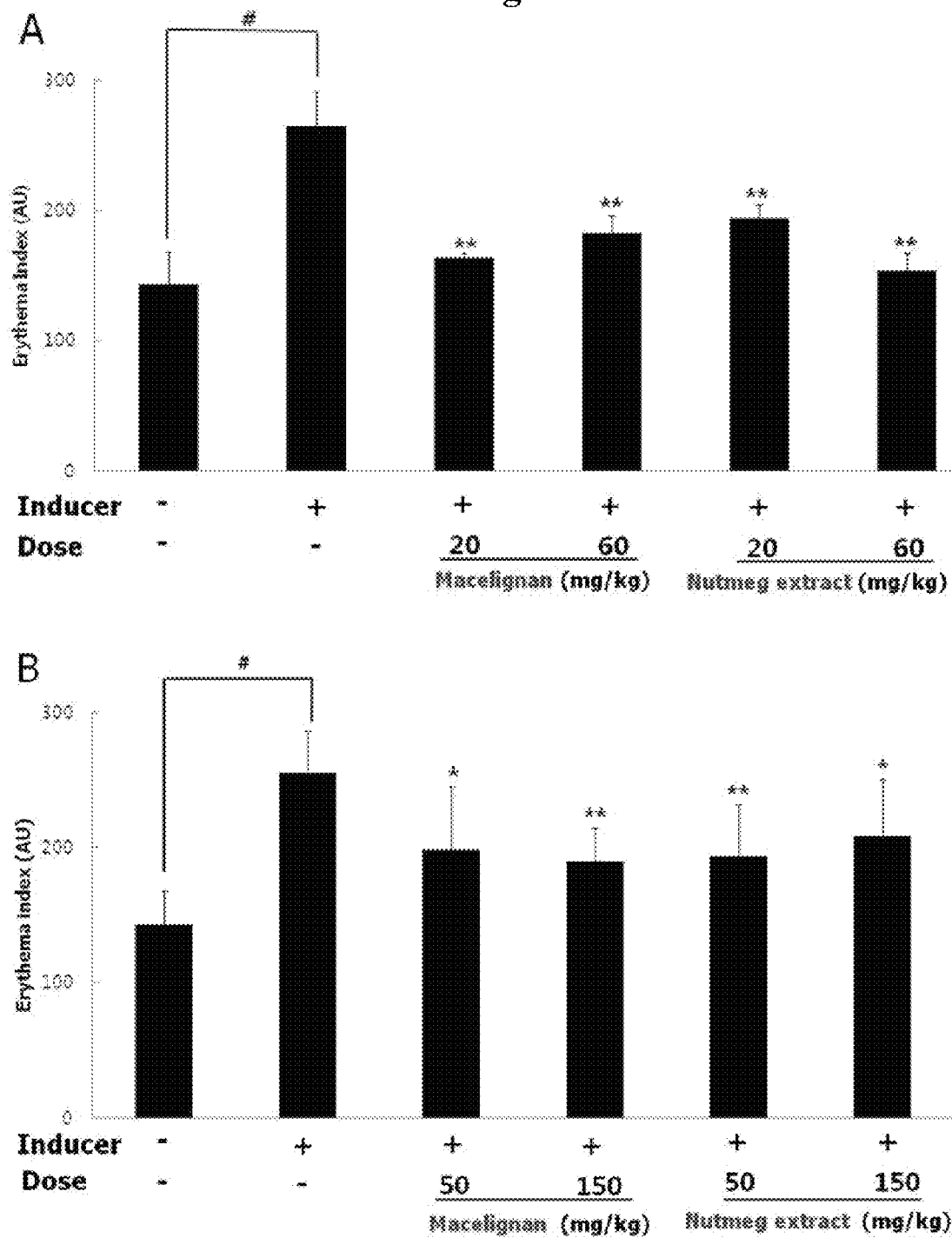
FIG. 21 shows the changes in erythema index by skin application (A) and oral administration (B) of macelignan and nutmeg extract.

The result of measuring erythema index is as seen in FIG. 21A and Table 16. The positive control group in which the NC/Nga had been treated with mite antigen cream for 5 weeks showed remarkably increased erythema index as compared to the negative control group. The ML-20, ML-60, NE-20 and NE-60 topical application groups showed statistically significant effect of decreasing erythema index as compared to the positive control group ($p<0.01$). Also, as seen in FIG. 21B and Table 17, the ML-50, ML-150, NE-50 and NE-150 oral administration groups showed statistically significant effect of decreasing erythema index as compared to the positive control group ($p<0.01$).

TABLE 16

Change in erythema index after topical application of macelignan and nutmeg extract

|  | Control (−) | Control (+) | ML-20 | ML-60 | NE-20 | NE-60 |
|---|---|---|---|---|---|---|
| Erythema Index | 148 ± 21 | 265 ± 26.4 | 163.3 ± 4.0 | 190 ± 24 | 193 ± 39 | 208.58 ± 42 |

TABLE 17

Change in erythema index after oral administration of macelignan and nutmeg extract

|  | Control (−) | Control (+) | ML-50 | ML-150 | NE-50 | NE-150 |
|---|---|---|---|---|---|---|
| Erythema Index | 138 ± 29 | 255.6 ± 30.1 | 198.5 ± 46.8 | 190 ± 24.4 | 193 ± 39.0 | 208.5 ± 42.6 |

<10-8> Immunohistochemical Staining

After the end of the experiment, skin was isolated from the occipital region. Hematoxylin/eosin (H&E) staining was performed to examine change of inflammatory cells such as mast cells, neutrophils, eosinophils, etc. in the epidermis, dermis and keratinocytes and change of skin thickness. Toluidine blue staining was performed to selectively stain the mast cells, and congo red staining was performed to selectively stain the eosinophils.

The result of H&E staining is as seen in FIG. 22A. The positive control group in which the NC/Nga had been treated with mite antigen cream for 5 weeks showed remarkably increased inflammatory cells and increased epidermal thickness as compared to the negative control group. The ML-20, ML-60, NE-20 and NE-60 topical application groups showed effect of decreasing inflammatory cells and increased epidermal thickness as compared to the positive control group. Also, as seen in FIG. 22B, the ML-50, ML-150, NE-50 and NE-150 oral administration groups showed effect of decreasing inflammatory cells and increased epidermal thickness as compared to the positive control group.

The result of Toluidine blue staining is as seen in FIG. 23A. The positive control group in which the NC/Nga had been treated with mite antigen cream for 5 weeks showed remarkably increased mast cells as compared to the negative control group. The ML-20, ML-60, NE-20 and NE-60 topical application groups showed effect of decreasing mast cells as compared to the positive control group. Also, as seen in FIG. 23B, the ML-50, ML-150, NE-50 and NE-150 oral administration groups showed effect of decreasing mast cells as compared to the positive control group.

The result of Congo red staining is as seen in FIG. 24A. The positive control group in which the NC/Nga had been treated with mite antigen cream for 5 weeks showed remarkably increased eosinophils as compared to the negative control group. The ML-20, ML-60, NE-20 and NE-60 topical application groups showed effect of decreasing eosinophils as compared to the positive control group. Also, as seen in FIG. 24B, the ML-50, ML-150, NE-50 and NE-150 oral administration groups showed effect of decreasing eosinophils as compared to the positive control group.

<10-9> Measurement of Cytokine Level in ALN (Axillary Lymph Node)

After the end of the experiment, ALN was separated and kept in DMEM containing 2% FBS at 4° C. The isolated ALN was passed through a cell strainer using the piston tip of a syringe and suspended in 5 mL of DMEM-10 (100 mL fetal bovine serum/1 L DMEM, Invitrogen Life Technologies, USA). The suspended cells were centrifuged at 13,000 rpm for 10 minutes and the resultant pellets were suspended in 1 mL of RBC lysis buffer (Biolegend, USA). After incubation for 5-10 minutes at room temperature, followed by addition of 9 mL of DMEM-10 and centrifuge at 13,000 rpm for 10 minutes, the resultant pellets were suspended in 3 mL of DMEM-10. The cells were seeded on a 24-well plate at $5 \times 10^5$ cells/mL and Dfb powder (Biostir, Inc., Japan) was added to each well to a working concentration of 1 μg/mL. 48 hours later, the supernatant was collected and subjected to analysis of cytokines in T cells and B cells by ELISA.

<10-10> Measurement of Cytokine Level in ALN

ALN is a immune organ that plays an important role in animal model of chronic atopic dermatitis. It is reported that some patients with severe atopic dermatitis have their armpits swollen and the size of ALN is increased. Of the NC/Nga mice treated with mite antigen cream, those having two or more ALNs were observed. Recently, ALN is studied in many researches about atopic dermatitis using NC/Nga mouse. In this experiment, the level of Th1/Th2 cell-related cytokines INF-γ and IL-4 was measured in ALN, which plays roles in immune response related local inflammation, thereby investigating the effect of the test sample on inflammation in skin lesion and Th1 cell activation in chronic atopic dermatitis.

<10-11> Measurement of IL-4 Level

IL-4 is a representative cytokine secreted by Th2 cells. In atopic dermatitis, it is known that IL-4 level is increased to activate inflammatory cells such as B cells, mast cells, macrophages, etc. Thus, IL-4 level in lymphocytes was measured to investigate the effect of the test sample on Th2 cells and inflammation. IL-4 level was measured from lymphocyte culture medium using a mouse IL-4 ELISA kit (ID Labs™ Inc., Canada).

Figure 25:
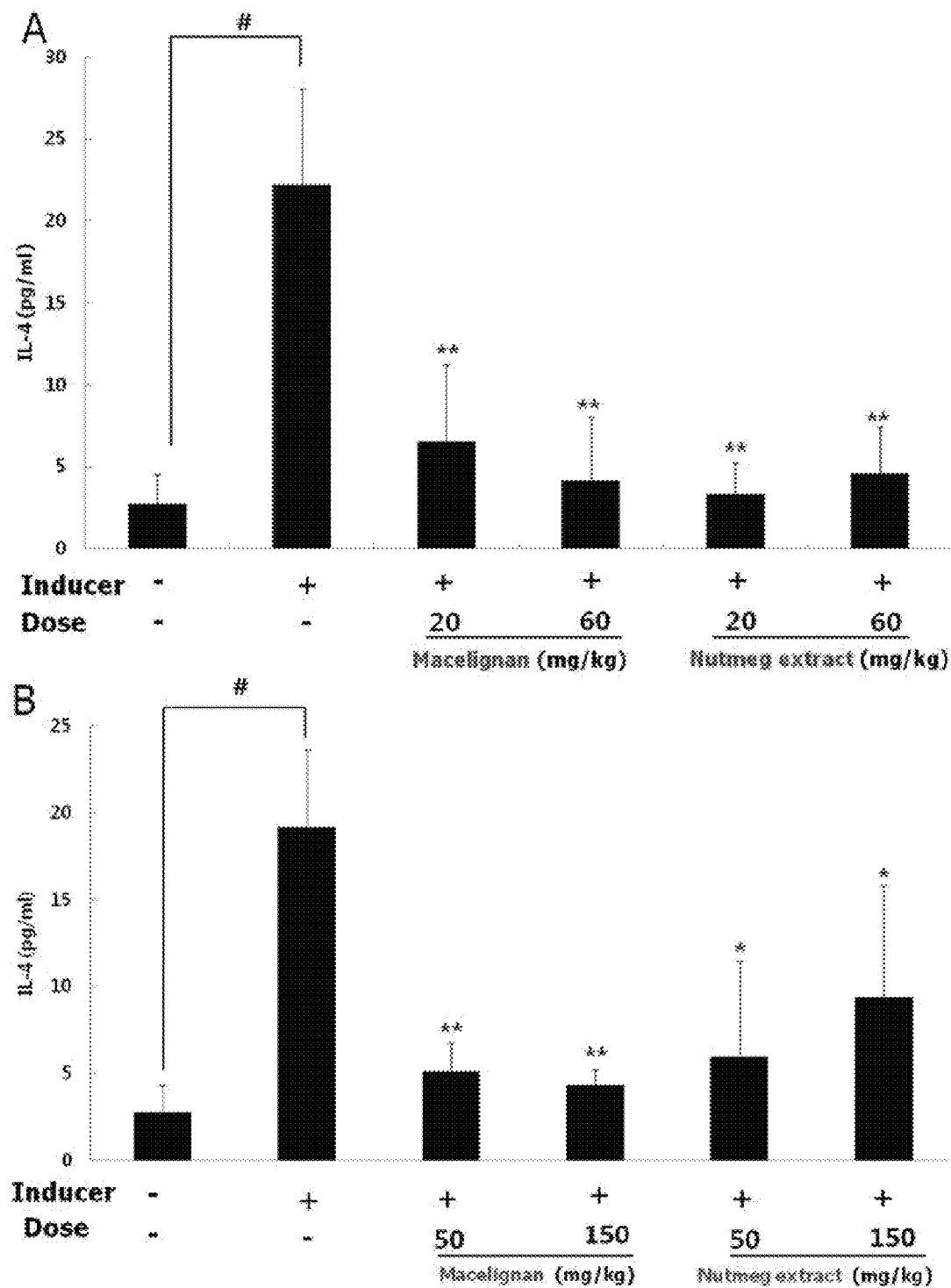
FIG. 25 shows the change in IL-4 level of ALN by skin application (A) and oral administration (B) of macelignan and nutmeg extract.

The result of measuring IL-4 level in ALN is as seen in FIG. 25A and Table 18. The positive control group in which the NC/Nga had been treated with mite antigen cream for 5 weeks showed remarkably increased IL-4 level as compared to the negative control group. The ML-20, ML-60, NE-20 and NE-60 topical application groups showed statistically significant effect of decreasing IL-4 level as compared to the positive control group ($p<0.01$). Also, as seen in FIG. 25B and Table 19, the ML-50, ML-150, NE-50 and NE-150 oral administration groups showed statistically significant effect of decreasing IL-4 level as compared to the positive control group ($p<0.01$).

TABLE 18

Change of IL-4 level in ALN after topical application of macelignan and nutmeg extract

|  | Control (−) | Control (+) | ML-20 | ML-60 | NE-20 | NE-60 |
|---|---|---|---|---|---|---|
| IL-4 (pg/ml) | 2.8 ± 1.8 | 22.2 ± 5.9 | 6.6 ± 4.7 | 4.2 ± 3.9 | 3.3 ± 1.9 | 4.6 ± 2.8 |

TABLE 19

Change of IL-4 level in ALN after oral administration of macelignan and nutmeg extract

|  | Control (−) | Control (+) | ML-50 | ML-150 | NE-50 | NE-150 |
|---|---|---|---|---|---|---|
| IL-4 (pg/ml) | 2.74 ± 1.6 | 19.2 ± 4.4 | 5.1 ± 1.6 | 4.3 ± 0.9 | 6.0 ± 5.5 | 9.4 ± 6.4 |

<10-12> Measurement of IFN-γ Level

IFN-γ, the representative cytokine secreted by Th1 cells, is known to decrease in level in atopic dermatitis, thereby activating Th2 cells. Thus, IFN-γ level in lymphocytes was measured to investigate the effect of the test sample on Th1 cells and inflammation. IFN-γ level was measured from lymphocyte culture medium using a mouse ELISA IFN-γ kit (Assay designs, Inc., Greece).

Figure 26:
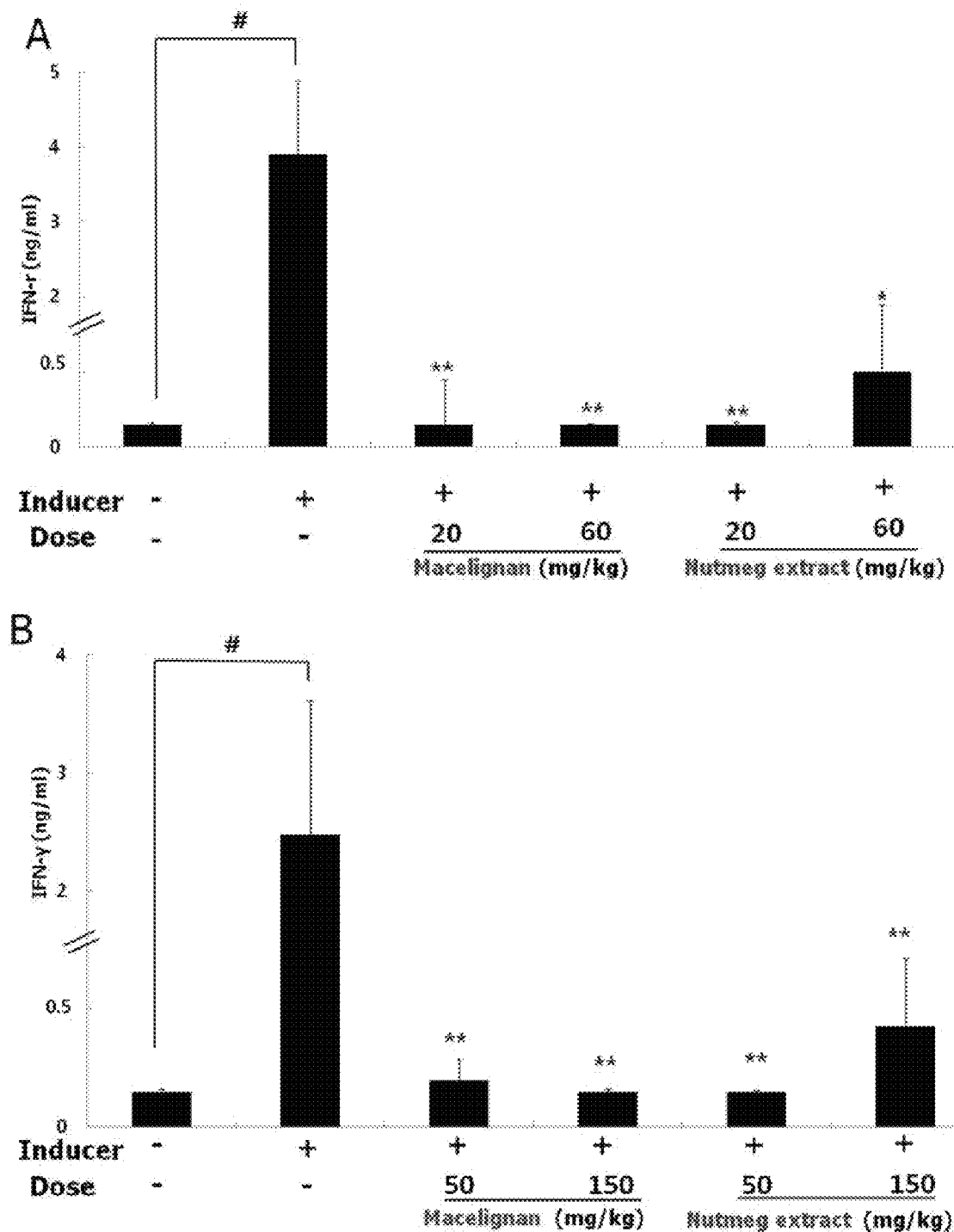
FIG. 26 shows the change in IFN-γ level of ALN by skin application (A) and oral administration (B) of macelignan and nutmeg extract.

The result of measuring IFN-γ level in ALN is as seen in FIG. 26A and Table 20. The positive control group in which the NC/Nga had been treated with mite antigen cream for 5 weeks showed remarkably increased IFN-γ level as compared to the negative control group. The ML-20, ML-60, NE-20 and NE-60 topical application groups showed statistically significant effect of decreasing IFN-γ as compared to the positive control group ($p<0.01$). Also, as seen in FIG. 26B and Table 21, the ML-50, ML-150, NE-50 and NE-150 oral administration groups showed statistically significant effect of decreasing IFN-γ level as compared to the positive control group ($p<0.01$).

TABLE 20

Change of IFN-γ level after topical application of macelignan and nutmeg extract

|  | Control (−) | Control (+) | ML-20 | ML-60 | NE-20 | NE-60 |
|---|---|---|---|---|---|---|
| IFN-γ (pg/ml) | 0.3 ± 0.025 | 3.9 ± 1.0 | 0.3 ± 0.6 | 0.3 ± 0.01 | 0.3 ± 0.03 | 1.0 ± 0.9 |

TABLE 21

Change of IFN-γ level after oral administration of macelignan and nutmeg extract

|  | Control (−) | Control (+) | ML-20 | ML-60 | NE-20 | NE-60 |
|---|---|---|---|---|---|---|
| IFN-γ (pg/ml) | 0.3 ± 0.04 | 2.5 ± 1.1 | 0.4 ± 0.2 | 0.3 ± 0.03 | 0.3 ± 0.01 | 0.9 ± 0.6 |

<10-13> Measurement of Inflammatory Cytokine mRNA Level in Skin Lesion

IL-13 is known to be secreted by Th2 cells, mast cells, or the like and be involved in dermatitis by affecting B cells, eosinophils, or the like. And, TNF-α is known to be secreted by inflammation-related cells such as mast cells and macrophages and be involved in chronic atopic dermatitis. Thus, mRNA level of IL-13 and TNF-α was measured by reverse transcription polymerase chain reaction (RT-PCR) in order to investigate the effect of the test sample on skin inflammation by atopic dermatitis and chronic atopic dermatitis.

<10-14> Isolation of RNA from Skin Tissue

After the end of the experiment, skin tissue was isolated from the occipital region to the back of the mouse, immersed in liquid nitrogen, pulverized using a mortar, dissolved in 500 μL of TRIzol® (InvitrogenLife Technologies, USA), and then homogenized using a homogenizer in order to measure mRNA level of cytokines in skin lesion. After adding chloroform (200 μL) and mixing for 15 seconds, the mixture was kept in ice for 3 minutes and centrifuged at 13,000 rpm for 15 minutes. After the centrifuge, the supernatant was moved to a fresh tube. After adding isopropanol (500 μL) and slowly shaking, the mixture was kept at room temperature for 10 minutes and then centrifuged at 13,000 rpm for 15 minutes. After the centrifuge, the supernatant was discarded and the remaining pellets were washed 2 times with 100% ethanol, dried, and then subjected to RNA quantification by spectrophotometry.

<10-15> RT-PCR

RT-PCR reaction is as follows: Total RNA (2 μg) was denatured at 70° C. for 5 minutes. The denatured RNA (16 μL) was added to reverse transcriptase premix (Elpis Biotech Inc., Korea) to make 20 μL. Then, cDNA was synthesized by carrying out reaction at 42° C. for 55 minutes, and then at 70° C. for 15 minutes. The synthesized cDNA was added to HiPi PCR premix (Elpis Biotech Inc., Korea) and subjected to PCR after adding primer and DEPC water to make a total volume of 20 μL. Reaction condition for IL-13 was pre-denaturation at 95° C. for 5 minutes, 35 cycles of denaturation at 95° C. for 30 seconds, annealing at 58° C. for 1 minute and elongation at 72° C. for 1 minute, followed by post-elongation at 72° C. for 5 minutes. Reaction condition for TNF-α was pre-denaturation at 95° C. for 5 minutes, 35 cycles of denaturation at 95° C. for 30 seconds, annealing at 64° C. for 1 minute and elongation at 72° C. for 1 minute, followed by post-elongation at 72° C. for 5 minutes. Each PCR product (5 μL) was electrophoresed on 1.5% agarose gel. The primers used are listed in Table 22.

TABLE 22

| Gene | Primer Sequence | |
|---|---|---|
| IL-13 | Forward 5'-GCTCTGGGCTTCATGGCGCT-3' | (SEQ ID NO: 1) |
|  | Reverse 5'-GAAGGGGCCGTGGCGAAACA-3' | (SEQ ID NO: 2) |
| TNF-α | Forward 5'-GCGGAGTCCGGGCAGGTCTA-3' | (SEQ ID NO: 3) |
|  | Reverse 5'-GGGGGCTGGCTCTGTGAGGA-3' | (SEQ ID NO: 4) |
| GAPDH | Forward 5'-CCCACTAACATCAAATGGGG-3' | (SEQ ID NO: 5) |
|  | Reverse 5'-ACACATTGGTAGGAACA-3' | (SEQ ID NO: 6) |

The result of investigation IL-13 mRNA level in skin lesion is as seen in FIG. 27A. The positive control group in which the NC/Nga had been treated with mite antigen cream for 5 weeks showed remarkably increased IL-13 mRNA level as compared to the negative control group. The ML-20, ML-60, NE-20 and NE-60 topical application groups showed effect of decreasing IL-13 mRNA level as compared to the positive control group. Also, as seen in FIG. 27B, the ML-50, ML-150, NE-50 and NE-150 oral administration groups showed statistically significant effect of decreasing IL-13 mRNA level as compared to the positive control group.

The result of investigation TNF-α mRNA level in skin lesion is as seen in FIG. 28A. The positive control group in which the NC/Nga had been treated with mite antigen cream for 5 weeks showed remarkably increased TNF-α mRNA level as compared to the negative control group. The ML-20, ML-60, NE-20 and NE-60 topical application groups showed effect of decreasing TNF-α mRNA level as compared to the positive control group. Also, as seen in FIG. 28B, the ML-50, ML-150, NE-50 and NE-150 oral administration groups showed statistically significant effect of decreasing TNF-α mRNA level as compared to the positive control group.

<10-16> Measurement of Level of Transcription Factors Involved in Th1/Th2 Modulation in Spleen T-bet, the representative transcription factor of Th1 cells, and GATA-3, the representative transcription factor of Th2 cells, are expressed competitively to regulate the cytokines produced by each T helper cells. Accordingly, they are key factors in the treatment of atopic dermatitis by Th1/Th2 modulation. The expression level of the representative transcription factors of Th1/Th2 cells in the spleen, which plays an important role in immune responses, was investigated in protein level.

After the end of the experiment, the spleen was extracted from the mouse and homogenized using a homogenizer in 500 μL of RIPA lysis buffer (Elpis Biotech Inc., Korea). After centrifuge at 13,000 rpm for 10 minutes, the supernatant was collected and subjected to protein quantification by Bradford assay. Expression level of T-bet and GATA-3 was measured using 40 μg of the protein, and primary antibody (rabbit anti-GATA-3 polyclonal antibody or rabbit anti-T-bet/Tbx21 polyclonal antibody, Abcam, UK) and secondary antibody (B ethyl Laboratories Inc., USA) by western blotting.

The result of measuring T-bet expression in spleen is as seen in FIG. 29A. The positive control group in which the NC/Nga had been treated with mite antigen cream for 5 weeks showed remarkably decreased T-bet expression level as compared to the negative control group. The ML-20, ML-60, NE-20 and NE-60 topical application groups showed effect of increasing T-bet expression level as compared to the positive control group. Also, as seen in FIG. 29B, the ML-50, ML-150, NE-50 and NE-150 oral administration groups showed statistically significant effect of increasing T-bet expression level as compared to the positive control group.

The result of measuring GATA-3 expression level in spleen is as seen in FIG. 30A. The positive control group in which the NC/Nga had been treated with mite antigen cream for 5 weeks showed remarkably increased GATA-3 expression level as compared to the negative control group. The ML-20, ML-60, NE-20 and NE-60 topical application groups showed effect of decreasing GATA-3 expression level as compared to the positive control group. Also, as seen in FIG. 30B, the ML-50, ML-150, NE-50 and NE-150 oral administration groups showed effect of decreasing GATA-3 expression level as compared to the positive control group.

<10-17> Clinical Visual Evaluation

Prior to the end of the experiment, the lesions of the mice were photographed. The change of the skin lesion was evaluated visually.

The result of clinical visual evaluation is as seen in FIG. 31A. The ML-20, ML-60, NE-20 and NE-60 topical application groups showed remarkable decrease in erythema/hemorrhage, dryness/scarring, edema, excoriation/erosion and lichenification and improvement in atopic dermatitis as compared to the positive control group. Also, as seen in FIG. 31B, the ML-50, ML-150, NE-50 and NE-150 oral administration groups showed remarkable decrease in erythema/hemorrhage, dryness/scarring, edema, excoriation/erosion and lichenification and improvement in atopic dermatitis as compared to the positive control group.

Example 11

Macelignan's Effect of Preventing/Treating Asthma

<11-1> Test Animals 7-week-old specific pathogen-free C57BL/6 (B6) male mice (20-25 g) were purchased from Jackson Laboratory and kept in an SPF facility of KAIST (Korea Advanced Institute of Science and Technology), at temperature 21-23° C., humidity 55-65%, and lighting intensity 150-300 lux. Water was given sufficiently and standard diet (PMI LabDiet) was provided.

<11-2> Sample Preparation

A single oral administration dose (300 μL) of macelignan in powder form was dissolved in corn oil, at low concentration (400 μg/g) and high concentration (800 μg/g).

<11-3> Inducing Asthma and Oral Administration of Macelignan

5 μL of allergen, AP (aspergillus protease, 1 mg/mL, Sigma-Aldrich, St. Louis, Mo.) was mixed with 45 μL of OVA (chicken egg ovalbumin, 0.5 mg/mL, Sigma-Aldrich). After 3 intraperitoneal injections with 4-day intervals, asthma was induced by 2 intranasal challenges with 4-day interval. The intranasal challenge was performed under isoflurane inhalational anesthesia. Macelignan dissolved in corn oil was orally administered every day.

<11-4> Evaluation of Effect of Macelignan

Within 24 hours after the last allergen challenge, the mouse was anesthetized by intraperitoneal injection of 0.1 mg/g sodium pentobarbital. After tracheal intubation, flexiVent (Scireq®, Montreal, Canada) was connected to maintain stable ventilation. Thereafter, striated muscle was relaxed by intravenous (IV) administration of 0.08 mg/kg pancuronium (Sigma-Aldrich). Following airway hypersensitivity test by IV administration of acetylcholine (Sigma-Aldrich), 1 mL of DPBS (Dulbecco's phosphate buffered saline) was injected twice into the intubation tube using a syringe for bronchioalveolar lavage. Thereafter, the chest was opened and the lungs were subjected to ELISpot assay. Symbols for the test groups are as follows: C=negative control, V=inducing asthma+oral administration of vehicle (corn oil), ML400: inducing asthma+oral administration of 400 μg/g macelignan, ML800: inducing asthma+oral administration of 800 μg/g macelignan.

<11-5> Airway Hypersensitivity Test

When compared with a normal mouse, a mouse in which asthma is induced has hypertrophic mucosa and airway smooth muscle, and shows high sensitivity to acetylcholine. For airway hypersensitivity test, the mouse was anesthetized using sodium pentobarbital and, after tracheal intubation, flexiVent was connected to maintain stable ventilation. Then, striated muscle was relaxed by IV administration of pancuronium in order to reduce the airway resistance measurement error caused by spontaneous breathing. Immediately after IV administration of acetylcholine, airway resistance was measured 3 times by snapshot. The mean value was recorded as airway resistance.

Figure 32:
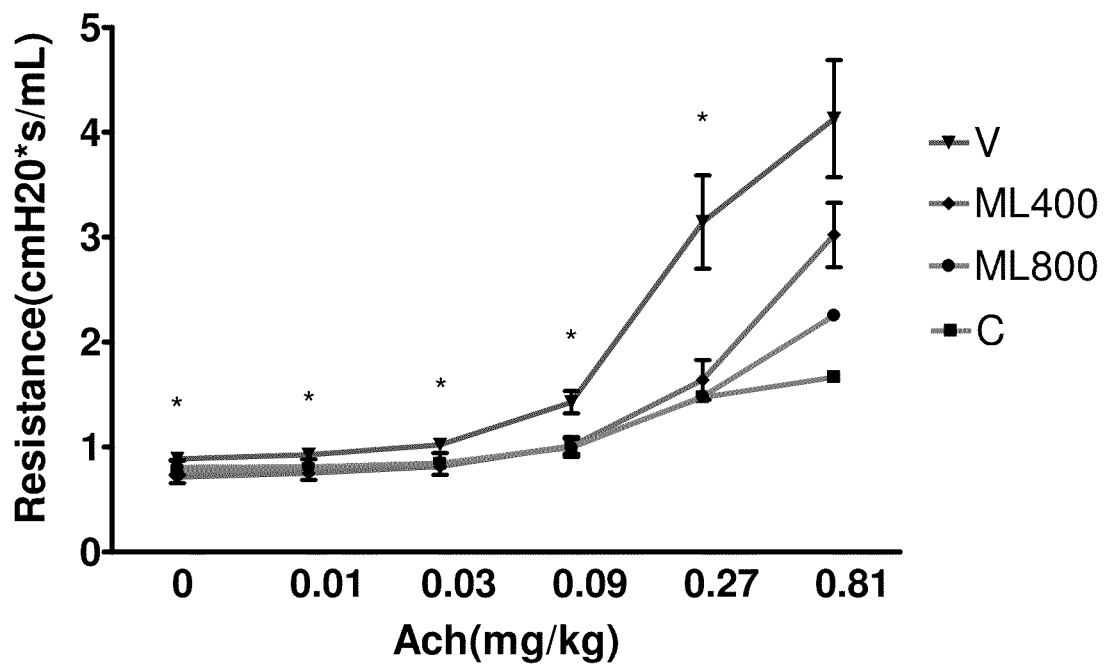
FIG. 32 shows the result of airway hypersensitivity test by the administration of macelignan

As seen in FIG. 32, the mouse in which asthma was induced showed increased airway hypersensitivity as compared to the negative control group. The group to which macelignan was orally administered showed statistically significant decrease of airway hypersensitivity as compared to the group to which vehicle (corn oil) was orally administered ($p<0.05$).

<11-6> Counting of Immune Cells in Bronchioalveolar Lavage (BAL) Fluid

When asthma is induced, various inflammatory cells increase in the airway. Especially, increased eosinophils are characteristic. After performing BAL by injecting 1 mL of DPBS into the intubation tube, the BAL fluid was collected. After performing BAL once again and collecting the BAL fluid, its volume was measured. After counting total immune cells in the BAL fluid using a hemocytometer, the cells were coated on a slide by cytospinning (400 rpm, 5 min). Then, differential immune cell containing was performed after Wright-Giemsa staining.

Figure 33:
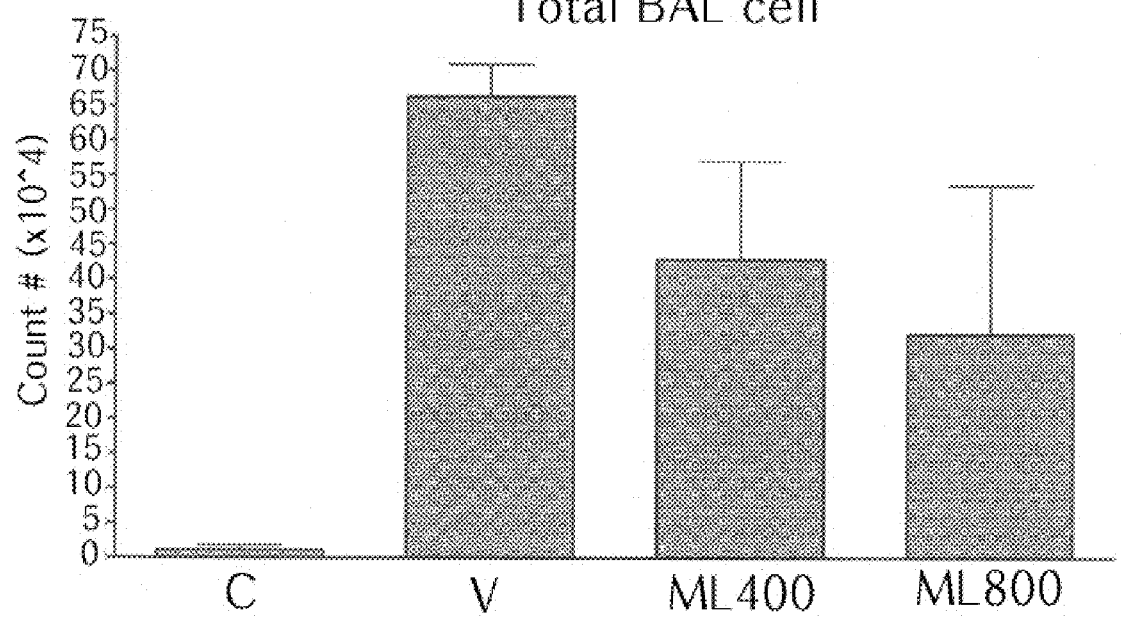
FIG. 33 shows the number of total immune cells in BAL fluid.
Figure 34:
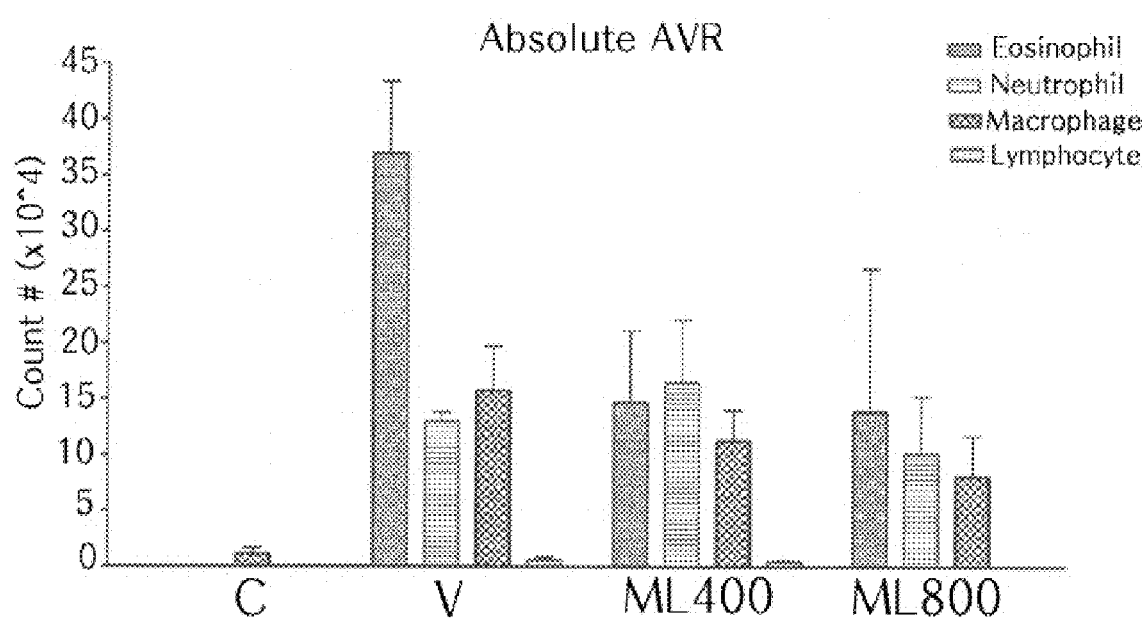
FIG. 34 shows the result of differential immune cell counting in BAL fluid.
Figure 35:
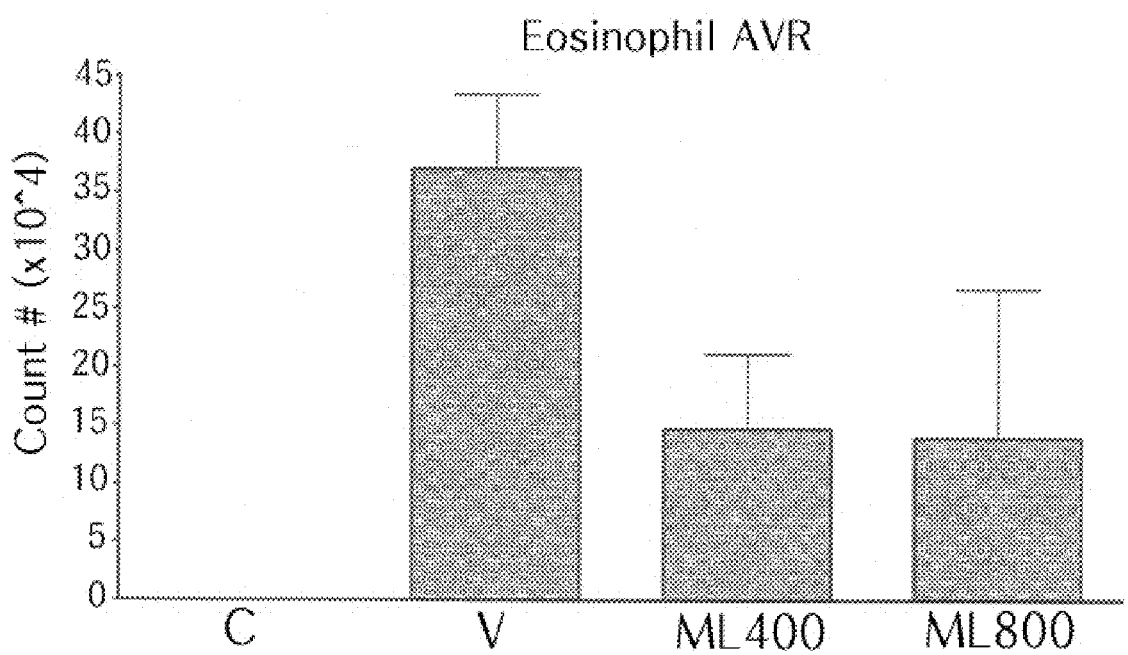
FIG. 35 shows the number of eosinophils in BAL fluid.

As seen in FIG. 33 to FIG. 35, the group in which asthma was induced showed increased total immune cells and eosinophils in the BAL fluid as compared to the negative control group. The groups to which macelignan was orally administered at 400 μg/g and 800 μg/g showed decreased eosinophils as compared to the group to which vehicle (corn oil) was orally administered. Decrease of other immune cells was not observed.

<11-7> Counting of IL-4 Secreting Cells in the Lungs

When asthma is induced in a mouse, Th2 cells in the lungs increase. Since Th2 cells secrete IL-4, ELISpot was performed to investigate it. One day prior to test, anti-mouse IL-4 antibody (BD PharMingen, San Diego, Calif.) was coated on an ELISA plate. The chest of the mouse was opened and the extracted lungs were pulverized using a cell strainer. Plate blocking had been performed previously and 100 µL of RPMI-CM had been added to each well of the ELISA plate. The total cells were centrifuged, re-suspended in 1 mL of RPMI complete medium, and added at 100 µL to each well. After overnight incubation, biotinylated anti-mouse IL-4 antibody (BD PharMingen) was attached, and then streptavidin-alkaline phosphatase (BD PharMingen) was attached. After addition of substrate dissolved in 0.6% low melting agarose followed by incubation at 4° C., spots were counted within 24 hours to count the number of IL-4 secreting cells in the lungs.

Figure 36:
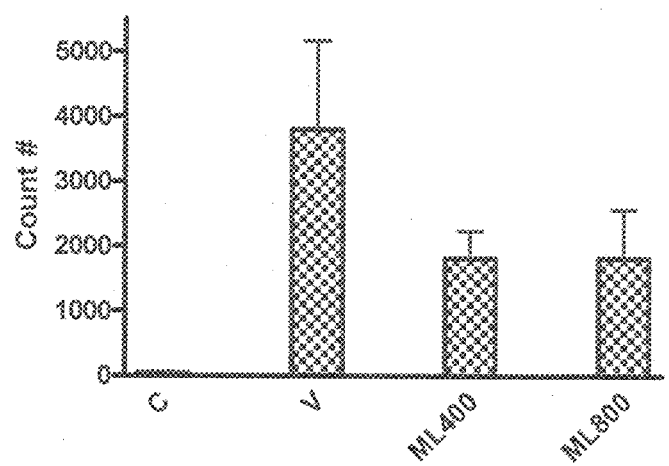
FIG. 36 shows the number of cell secreting IL-4.

As seen in FIG. 36, increase of IL-4 secreting cells was observed in the lungs of the mouse in which asthma was induced as compared to the negative control group. The groups to which macelignan was orally administered at 400 µg/g and 800 µg/g showed decreased IL-4 secreting cells as compared to the group to which vehicle (corn oil) was orally administered.

<11-8> Measurement of Glycoprotein Level in BAL Fluid

When asthma is induced, secretion of mucin increases in the airway. Glycoprotein ELISA was carried out to quantitate mucin in BAL fluid. After performing BAL by injecting 1 mL of DPBS into the intubation tube, the BAL fluid was collected. After performing BAL once again and collecting the BAL fluid, centrifuge (4° C., 1200 rpm, 5 min) was carried out. Thus obtained supernatant was diluted to 1:100 with DPBS and coated on an ELISA plate along with standard solution. After blocking, followed by treating with biotinylated jacalin and then with streptavidin-alkaline phosphatase, substrate was added and absorbance was measured at 405 nm Glycoprotein level in the BAL fluid was determined by comparing with the standard curve obtained using the standard solution.

Figure 37:
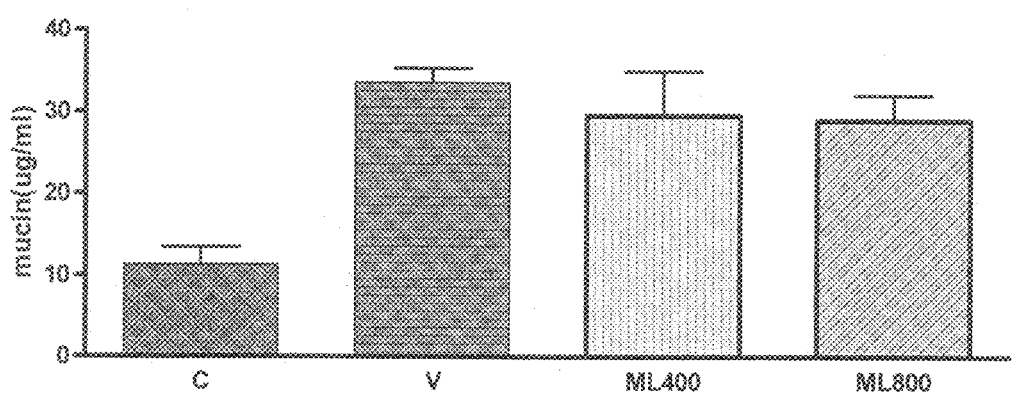
FIG. 37 shows the amount of glycoproteins in BAL fluid.

As seen in FIG. 37, the group in which asthma was induced showed increased glycoprotein level in the BAL fluid as compared to the negative control group. The groups to which macelignan was orally administered at 400 µg/g and 800 µg/g showed decreased glycoprotein level.

Preparation Example 1

Preparation of Pharmaceutical Formulations Comprising Inventive Pharmaceutical Composition for Treating or Preventing Inflammatory Disease <1-1> Preparation of Tablet Formulation 25 mg of the inventive lignan compound or *Myristica fragrans* extract, 26 mg of lactose for direct tableting, 3.5 mg of Avicel (microcrystalline cellulose), 15 mg of disintegration aid sodium starch glyconate and 8 mg of binder L-HPC (low-hydroxypropylcellulose) for direct tableting were placed and mixed with each other in U-type mixer for 20 minutes. After completion of the mixing, 1 mg of lubricant magnesium stearate was further added thereto and mixed for 3 minutes. The mixture was subjected to test for quantitative analysis and moisture content analysis, tableted and coated with a film, thus preparing a tablet formulation.

<1-2> Preparation of Syrup

A syrup comprising 2% (w/v) of the inventive macelignan or its pharmaceutically acceptable salt as an active ingredient was prepared in the following manner:

2 g of an acid addition salt of the inventive macelignan, 0.8 g of saccharin and 25.4 g of sugar were dissolved in 80 g of hot water. The solution was cooled, to which 8.0 g of glycerin, 0.04 g of fragrance, 4.0 g of ethanol, 0.4 g of sorbic acid and a suitable amount of distilled water were then added. To the mixture, water was added to make a volume of 100 ml.

<1-3> Preparation of Capsule Formulation 50 mg of the inventive lignan compound or *Myristica fragrans* extract, 50 mg of lactose, 46.5 mg of starch, 1 mg of talc and a suitable amount of magnesium stearate were mixed with each other. The mixture was filled in a hard gelatin capsule, thus preparing a capsule formulation.

<1-4> Preparation of Injectable Liquid

An injectable liquid comprising 10 mg of the active ingredient was prepared in the following manner:

1 g of a hydrochloride of the inventive macelignan, 0.6 g of sodium chloride and 0.1 g of ascorbic acid were dissolved in distilled water to make 100 ml of a solution. The solution was bottled and sterilized by heating it at 20° C. for 30 minutes.

Application Example 1

Gastric Inflammatory Digestive Diseases

It was known that gastric inflammation is mainly caused by *Helicobacter pylori* infection, although various external factors and irregular eating habits are involved therein. *Helicobacter pylori* causes not only gastric ulcer and gastritis, but also gastric cancer. During the proliferation of *Helicobacter pylori*, enzyme COX-2 (cyclooxygenase-2) also increases at the same time (Nam N. T. et al., *Clin. Cancer Res.* 10(23): 8105-8113, 2004). It was known that, when infected with *Helicobacter pylori*, gastric mucosal cells proliferate into cancer cells; COX-2 inhibitors suppress the growth and proliferation of gastric mucosal cells into cancer cells and inhibit normal tissue from changing into cancer tissue. It was found that a group administered with the COX-2 inhibitor is superior to a group administered with no COX-2 inhibitor in the effect of killing cancer tissue by an apoptosis method (Nam N. T. et al., Clin. Cancer Res. 10(23): 8105-8113, 2004). Accordingly, the COX-2 inhibitory effect of the inventive lignan compound suggests that the inventive lignan compound has a sufficient therapeutic effect, because it helps to treat gastric inflammation so as to be able to prevent gastric cancer in an early stage.

Application Example 2

Arthritis

Arthritis is caused by autoimmune abnormality, but chronic inflammation occurring in the synovial cavity between joints during the progression of arthritis induces angiogenesis so as to destroy cartilage. Arthritis includes infectious arthritis, degenerative arthritis, rheumatoid arthritis, and arthritis caused by avascular necrosis of femoral head, ankylosing spondylitis and congenital malformation. Regardless of the cause of arthritis, the chronic inflammation formed in the synovial cavity between joints during the progression of arthritis is known to induce angiogenesis and is characterized by invading joints with a new capillary vessel to cause damage to cartilage (Kocb A. E. et al., *Arth. Rheum.*, 29:471-479, 1986; Stupack D. G. et al., *J. Med. Biol. Rcs.*, 32:578-281, 1999; Koch A. E., *Arthritis Rheum.*, 41:951-962, 1998). In this case, it is reported that an inflammatory response, which occurs in several steps depending on the kind of diseases to destroy cartilage, plays an important role in the progression of the disease, and the formation of angiogenesis into joints acts as an important pathological mechanism (Colville-Nash, P. R. et al., *Ann. Rheum. Dis.*, 51, 919-925, 1992; Eisenstein, R., *Pharmacol. Ther.*, 49:1-19, 1991). For the treatment of arthritis, it is preferred to inhibit pain and a state of inflammation rather than to treat by causing, so as to reduce the destruction rate of joints or muscles and minimize the loss of their function. Accordingly, the inventive lignan compound or *Myristica fragrans* extract is highly effective in the prevention of arthritis progression and in the treatment of arthritis.

INDUSTRIAL APPLICABILITY

As described above, the inventive lignan compound has the effect of inhibiting inflammation reactions by inhibiting the production or expression of inflammation mediators NO, iNOS, $PGE_2$, COX-2 and TNF-α and by treating or preventing inflammatory disease in vivo. Accordingly, the inventive lignan compound or *Myristica fragrans* extract will be highly useful for the treatment or prevention of inflammatory diseases.

The invention claimed is:

1. A method for treating an inflammatory disease, comprising administering to a subject in need thereof an effective amount of macelignan represented by Chemical Formula I or a pharmaceutically acceptable salt thereof:

[Chemical Formula I]

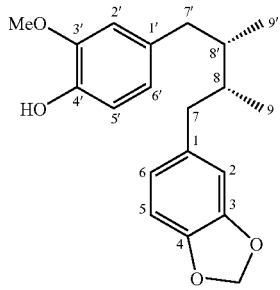

wherein the inflammatory disease is selected from the group consisting of osteoarthritis, infectious arthritis, post-infectious arthritis, gonococcal arthritis, tuberculous arthritis, viral arthritis, fungal arthritis, syphilitic arthritis, Lyme disease, arthritis associated with "vasculitic syndromes", non-articular rheumatism, rheumatoid arthritis, bronchial asthma, asthma and atopic dermatitis.

* * * * *

SEQUENCE LISTING

<160> NUMBER OF SEQ ID NOS: 6

<210> SEQ ID NO 1
<211> LENGTH: 20
<212> TYPE: DNA
<213> ORGANISM: IL-13

<400> SEQUENCE: 1
gctctgggct tcatggcgct          20

<210> SEQ ID NO 2
<211> LENGTH: 20
<212> TYPE: DNA
<213> ORGANISM: IL-13

<400> SEQUENCE: 2
gaaggggccg tggcgaaaca          20

<210> SEQ ID NO 3
<211> LENGTH: 20
<212> TYPE: DNA
<213> ORGANISM: TNF-alpha

<400> SEQUENCE: 3
gcggagtccg ggcaggtcta          20

<210> SEQ ID NO 4
<211> LENGTH: 20
<212> TYPE: DNA
<213> ORGANISM: TNF-alpha

<400> SEQUENCE: 4
gggggctggc tctgtgagga          20

<210> SEQ ID NO 5
<211> LENGTH: 20
<212> TYPE: DNA
<213> ORGANISM: GAPDH

<400> SEQUENCE: 5
cccactaaca tcaaatgggg          20

<210> SEQ ID NO 6
<211> LENGTH: 17
<212> TYPE: DNA
<213> ORGANISM: GAPDH

<400> SEQUENCE: 6
acacattggt aggaaca             17